United States Patent
Wang

(10) Patent No.: US 7,745,600 B2
(45) Date of Patent: Jun. 29, 2010

(54) ISOLATED NUCLEIC ACIDS FOR MUTANT MAMMALIAN NAV 1 PROTEINS

(75) Inventor: Sho-Ya Wang, Voorheesville, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/507,232

(22) Filed: Aug. 21, 2006

(65) Prior Publication Data

US 2007/0141640 A1 Jun. 21, 2007

Related U.S. Application Data

(63) Continuation of application No. 10/918,332, filed on Aug. 13, 2004, now Pat. No. 7,094,600, which is a continuation-in-part of application No. 10/608,584, filed on Jun. 26, 2003, now Pat. No. 7,087,374.

(51) Int. Cl.
*C07H 21/04* (2006.01)
*C12N 15/11* (2006.01)

(52) U.S. Cl. ............... 536/23.5; 435/91.1; 435/442

(58) Field of Classification Search ............ None
See application file for complete search history.

(56) References Cited

U.S. PATENT DOCUMENTS 7,087,374 B2   8/2006  Wang ................. 435/4
7,094,600 B2   8/2006  Wang ................. 435/369

OTHER PUBLICATIONS

Wells, Biochemistry 29:8509-8517, 1990.*
Ogata and Ohishi, J. Pharmacol. 88: 365-377, 2002.*
Godwin et al., Biophys. Chem. 113: 1-7, 2005.*
Felipe et al., J. Biol. Chem. 269: 30125-30131,1994.*
Wang et al., "A Phenylalanine Residue at Segment D3-S6 in Nav1.4 Voltage-Gated Na$^+$Channels Is Critical for Pyrethroid Action," Mol Pharmacol 60(3):620-628, 2001.
Wang et al., "State-dependent block of voltages-gated Na$^+$channels by amitriptyline via the local anesthetic receptor and its implication for neuropathic pain," PAIN 1-9; 2004.
Grant et al., "Block of Wild-Type and Inactivation-Deficient Cardiac Sodium Channels IFM/QQQ Stably Expressed in Mammalian Cells,".
Wang et al., "Mexiletine block of wild-type and inactivation-deficient human skeletal muscle hNav1.4 Na$^+$channels", J. Physiol. 2004, 554(Pt 3) 621-633.
Grant et al., "Block of Wild-Type and Inactivation-Deficient Cardiac Sodium Channels IFM/QQQ Stably Expressed in Mammalian Cells,", Biophys, 79: 3019-3035, 2000.

* cited by examiner

*Primary Examiner*—Robert Landsman
*Assistant Examiner*—Gyan Chandra
(74) *Attorney, Agent, or Firm*—Heslin Rothenberg Farley & Mesiti P.C.

(57) ABSTRACT

A method or screen for assessing the potential of a compound to treat a pathological condition, such as arrhythmia, which is manifested by an increased late sodium current in a heart is disclosed. The method employs a mutant sodium channel protein having an amino acid sequence in which one or more amino acids among the ten amino acids occurring at the carboxy end of the S6 segments of D1, D2, D3 or D4 domains of mammalian Nav1 differs from the amino acid in wild-type Nav1 by substitution with tryptophan, phenylalanine, tyrosine or cysteine. Cells transfected with a nucleic acid that encodes a mutant mammalian Nav1 protein, as well as isolated nucleic acid comprising a nucleotide sequence that codes for a mutant mammalian Nav1 protein are disclosed.

2 Claims, 19 Drawing Sheets

Fig. 2A
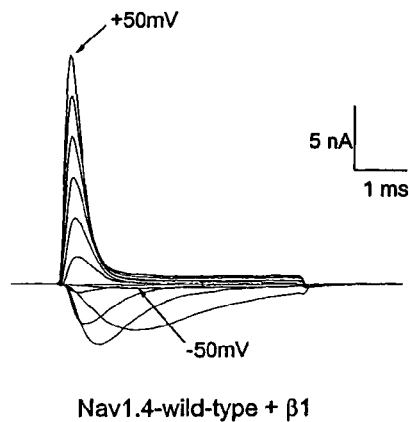
Nav1.4-wild-type + β1
Fig. 2B
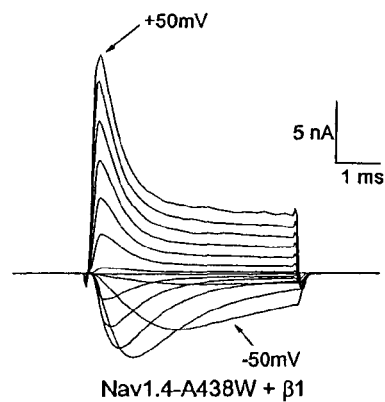
Nav1.4-A438W + β1
Fig. 2C
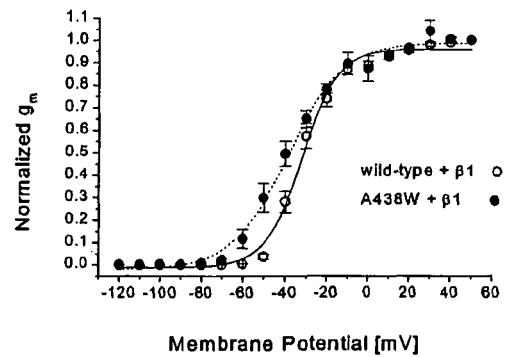
FIGURE 2

Fig. 5A
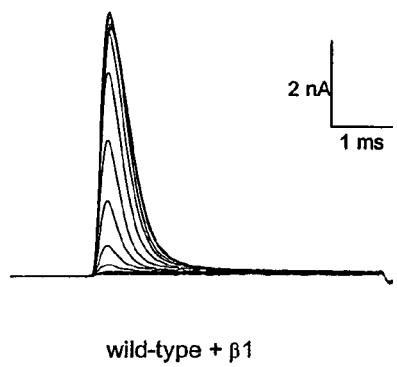
wild-type + β1
Fig. 5B
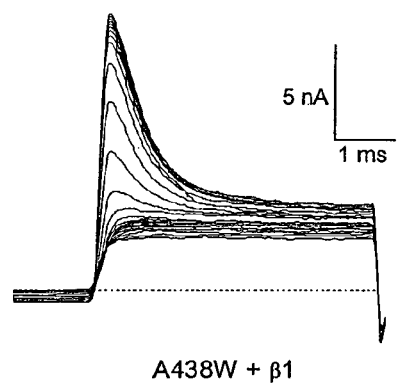
A438W + β1
Fig. 5C
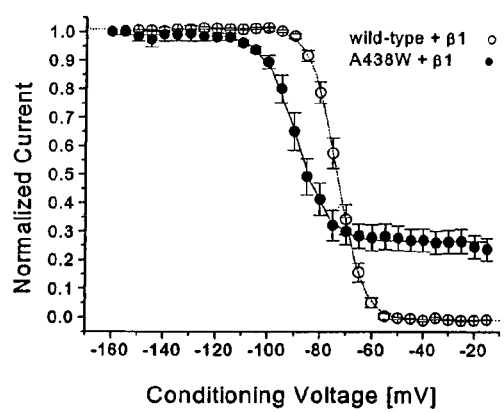
FIGURE 5

SEQUENCE LISTING

```
<160> NUMBER OF SEQ ID NOS: 78

<210> SEQ ID NO 1
<211> LENGTH: 28
<212> TYPE: PRT
<213> ORGANISM: Homo sapiens

<400> SEQUENCE: 1

Tyr Met Ile Phe Phe Val Leu Val Ile Phe Leu Gly Ser Phe Tyr Leu
 1               5                  10                  15

Ile Asn Leu Ile Leu Ala Val Val Ala Met Ala Tyr
            20                  25

<210> SEQ ID NO 2
<211> LENGTH: 28
<212> TYPE: PRT
<213> ORGANISM: Homo sapiens

<400> SEQUENCE: 2

Tyr Met Ile Phe Phe Val Leu Val Ile Phe Leu Gly Ser Phe Tyr Leu
 1               5                  10                  15

Ile Asn Leu Ile Leu Ala Val Val Ala Met Ala Tyr
            20                  25

<210> SEQ ID NO 3
<211> LENGTH: 28
<212> TYPE: PRT
<213> ORGANISM: Homo sapiens

<400> SEQUENCE: 3

Tyr Met Ile Phe Phe Val Leu Val Ile Phe Leu Gly Ser Phe Tyr Leu
 1               5                  10                  15

Ile Asn Leu Ile Leu Ala Val Val Ala Met Ala Tyr
            20                  25

<210> SEQ ID NO 4
<211> LENGTH: 28
<212> TYPE: PRT
<213> ORGANISM: Homo sapiens
```

-continued

<400> SEQUENCE: 4

Tyr Met Ile Phe Phe Val Val Ile Phe Leu Gly Ser Phe Tyr Leu
1               5                   10                  15

Ile Asn Leu Ile Leu Ala Val Val Ala Met Ala Tyr
            20                  25

<210> SEQ ID NO 5
<211> LENGTH: 28
<212> TYPE: PRT
<213> ORGANISM: Homo sapiens

<400> SEQUENCE: 5

Tyr Met Ile Phe Phe Met Leu Val Ile Phe Leu Gly Ser Phe Tyr Leu
1               5                   10                  15

Val Asn Leu Ile Leu Ala Val Val Ala Met Ala Tyr
            20                  25

<210> SEQ ID NO 6
<211> LENGTH: 28
<212> TYPE: PRT
<213> ORGANISM: Homo sapiens

<400> SEQUENCE: 6

Tyr Met Ile Phe Phe Val Val Val Ile Phe Leu Gly Ser Phe Tyr Leu
1               5                   10                  15

Val Asn Leu Ile Leu Ala Val Val Ala Met Ala Tyr
            20                  25

<210> SEQ ID NO 7
<211> LENGTH: 28
<212> TYPE: PRT
<213> ORGANISM: Homo sapiens

<400> SEQUENCE: 7

Tyr Met Ile Phe Phe Val Val Ile Phe Leu Gly Ser Phe Tyr Leu
1               5                   10                  15

Ile Asn Leu Ile Leu Ala Val Val Ala Met Ala Tyr
            20                  25

<210> SEQ ID NO 8
<211> LENGTH: 28
<212> TYPE: PRT
<213> ORGANISM: Rattus sp.

<400> SEQUENCE: 8

Tyr Met Ile Phe Phe Val Val Ile Phe Leu Gly Ser Phe Tyr Leu
1               5                   10                  15

Ile Asn Leu Ile Leu Ala Val Val Ala Met Ala Tyr
            20                  25

<210> SEQ ID NO 9
<211> LENGTH: 28
<212> TYPE: PRT
<213> ORGANISM: Rattus sp.

<400> SEQUENCE: 9

Tyr Met Ile Phe Phe Met Leu Val Ile Phe Leu Gly Ser Phe Tyr Leu
1               5                   10                  15

Val Asn Leu Ile Leu Ala Val Val Ala Met Ala Tyr
            20                  25

-continued

<210> SEQ ID NO 10
<211> LENGTH: 28
<212> TYPE: PRT
<213> ORGANISM: Rattus sp.

<400> SEQUENCE: 10

Tyr Met Ile Phe Phe Met Leu Val Ile Phe Val Gly Ser Phe Tyr Pro
 1               5                   10                  15

Val Asn Leu Ile Leu Ala Val Val Ala Met Ala Tyr
            20                  25

<210> SEQ ID NO 11
<211> LENGTH: 28
<212> TYPE: PRT
<213> ORGANISM: Rattus sp.

<400> SEQUENCE: 11

Tyr Met Val Phe Phe Val Val Val Ile Phe Leu Gly Ser Phe Tyr Leu
 1               5                   10                  15

Val Asn Leu Ile Leu Ala Val Val Ala Met Ala Tyr
            20                  25

<210> SEQ ID NO 12
<211> LENGTH: 28
<212> TYPE: PRT
<213> ORGANISM: Rattus sp.

<400> SEQUENCE: 12

Tyr Met Val Phe Phe Met Leu Val Ile Phe Leu Gly Ser Phe Tyr Leu
 1               5                   10                  15

Val Asn Leu Ile Leu Ala Val Val Ala Met Ala Tyr
            20                  25

<210> SEQ ID NO 13
<211> LENGTH: 28
<212> TYPE: PRT
<213> ORGANISM: Homo sapiens

<400> SEQUENCE: 13

Cys Leu Thr Val Phe Met Met Val Met Val Ile Gly Asn Leu Val Val
 1               5                   10                  15

Leu Asn Leu Phe Leu Ala Leu Leu Leu Ser Ser Phe
            20                  25

<210> SEQ ID NO 14
<211> LENGTH: 28
<212> TYPE: PRT
<213> ORGANISM: Homo sapiens

<400> SEQUENCE: 14

Cys Leu Thr Val Phe Met Met Val Met Val Ile Gly Asn Leu Val Val
 1               5                   10                  15

Leu Asn Leu Phe Leu Ala Leu Leu Leu Ser Ser Phe
            20                  25

<210> SEQ ID NO 15
<211> LENGTH: 28
<212> TYPE: PRT
<213> ORGANISM: Homo sapiens

```
<400> SEQUENCE: 15

Cys Leu Ile Val Phe Met Leu Val Met Val Ile Gly Asn Leu Val Val
 1               5                  10                  15

Leu Asn Leu Phe Leu Ala Leu Leu Ser Ser Phe
            20                  25

<210> SEQ ID NO 16
<211> LENGTH: 28
<212> TYPE: PRT
<213> ORGANISM: Homo sapiens

<400> SEQUENCE: 16

Cys Leu Leu Val Phe Leu Leu Val Met Val Ile Gly Asn Leu Val Val
 1               5                  10                  15

Leu Asn Leu Phe Leu Ala Leu Leu Ser Ser Phe
            20                  25

<210> SEQ ID NO 17
<211> LENGTH: 28
<212> TYPE: PRT
<213> ORGANISM: Rattus sp.

<400> SEQUENCE: 17

Cys Leu Thr Val Phe Leu Met Val Met Val Ile Gly Asn Leu Val Val
 1               5                  10                  15

Leu Asn Leu Phe Leu Ala Leu Leu Ser Ser Phe
            20                  25

<210> SEQ ID NO 18
<211> LENGTH: 28
<212> TYPE: PRT
<213> ORGANISM: Rattus sp.

<400> SEQUENCE: 18

Cys Leu Leu Val Phe Leu Leu Val Met Val Ile Gly Asn Leu Val Val
 1               5                  10                  15

Leu Asn Leu Phe Leu Ala Leu Leu Ser Ser Phe
            20                  25

<210> SEQ ID NO 19
<211> LENGTH: 28
<212> TYPE: PRT
<213> ORGANISM: Homo sapiens

<400> SEQUENCE: 19

Met Tyr Leu Tyr Phe Val Ile Phe Ile Ile Phe Gly Ser Phe Phe Thr
 1               5                  10                  15

Leu Asn Leu Phe Ile Gly Val Ile Ile Asp Asn Phe
            20                  25

<210> SEQ ID NO 20
<211> LENGTH: 28
<212> TYPE: PRT
<213> ORGANISM: Homo sapiens

<400> SEQUENCE: 20

Met Tyr Leu Tyr Phe Val Ile Phe Ile Ile Phe Gly Ser Phe Phe Thr
 1               5                  10                  15

Leu Asn Leu Phe Ile Gly Val Ile Ile Asp Asn Phe
            20                  25
```

```
<210> SEQ ID NO 21
<211> LENGTH: 28
<212> TYPE: PRT
<213> ORGANISM: Homo sapiens

<400> SEQUENCE: 21

Met Tyr Leu Tyr Phe Val Ile Phe Ile Ile Phe Gly Ser Phe Phe Thr
  1               5                  10                  15

Leu Asn Leu Phe Ile Gly Val Ile Ile Asp Asn Phe
             20                  25

<210> SEQ ID NO 22
<211> LENGTH: 28
<212> TYPE: PRT
<213> ORGANISM: Homo sapiens

<400> SEQUENCE: 22

Met Tyr Leu Tyr Phe Val Ile Phe Ile Ile Phe Gly Ser Phe Phe Thr
  1               5                  10                  15

Leu Asn Leu Phe Ile Gly Val Ile Ile Asp Asn Phe
             20                  25

<210> SEQ ID NO 23
<211> LENGTH: 28
<212> TYPE: PRT
<213> ORGANISM: Homo sapiens

<400> SEQUENCE: 23

Met Tyr Ile Tyr Phe Val Ile Phe Ile Ile Phe Gly Ser Phe Phe Thr
  1               5                  10                  15

Leu Asn Leu Phe Ile Gly Val Ile Ile Asp Asn Phe
             20                  25

<210> SEQ ID NO 24
<211> LENGTH: 28
<212> TYPE: PRT
<213> ORGANISM: Homo sapiens

<400> SEQUENCE: 24

Met Tyr Leu Tyr Phe Val Ile Phe Ile Ile Gly Gly Ser Phe Phe Thr
  1               5                  10                  15

Leu Asn Leu Phe Val Gly Val Ile Ile Asp Asn Phe
             20                  25

<210> SEQ ID NO 25
<211> LENGTH: 28
<212> TYPE: PRT
<213> ORGANISM: Rattus sp.

<400> SEQUENCE: 25

Met Tyr Leu Tyr Phe Val Ile Phe Ile Ile Phe Gly Ser Phe Phe Thr
  1               5                  10                  15

Leu Asn Leu Phe Ile Gly Val Ile Ile Asp Asn Phe
             20                  25

<210> SEQ ID NO 26
<211> LENGTH: 28
<212> TYPE: PRT
<213> ORGANISM: Rattus sp.
```

```
<400> SEQUENCE: 26

Met Tyr Ile Tyr Phe Val Val Phe Ile Ile Phe Gly Ser Phe Phe Thr
 1               5                  10                  15

Leu Asn Leu Phe Ile Gly Val Ile Ile Asp Asn Phe
            20                  25

<210> SEQ ID NO 27
<211> LENGTH: 28
<212> TYPE: PRT
<213> ORGANISM: Rattus sp.

<400> SEQUENCE: 27

Met Tyr Leu Tyr Phe Val Val Phe Ile Ile Phe Gly Ser Phe Phe Thr
 1               5                  10                  15

Leu Asn Leu Phe Ile Gly Val Ile Ile Asp Asn Phe
            20                  25

<210> SEQ ID NO 28
<211> LENGTH: 28
<212> TYPE: PRT
<213> ORGANISM: Rattus sp.

<400> SEQUENCE: 28

Met Tyr Ile Tyr Phe Val Val Phe Ile Ile Phe Gly Gly Phe Phe Thr
 1               5                  10                  15

Leu Asn Leu Phe Val Gly Val Ile Ile Asp Asn Phe
            20                  25

<210> SEQ ID NO 29
<211> LENGTH: 28
<212> TYPE: PRT
<213> ORGANISM: Homo sapiens

<400> SEQUENCE: 29

Gly Ile Phe Phe Phe Val Ser Tyr Ile Ile Ile Ser Phe Leu Val Val
 1               5                  10                  15

Val Asn Met Tyr Ile Ala Val Ile Leu Glu Asn Phe
            20                  25

<210> SEQ ID NO 30
<211> LENGTH: 28
<212> TYPE: PRT
<213> ORGANISM: Homo sapiens

<400> SEQUENCE: 30

Gly Ile Phe Phe Phe Val Ser Tyr Ile Ile Ile Ser Phe Leu Val Val
 1               5                  10                  15

Val Asn Met Tyr Ile Ala Val Ile Leu Glu Asn Phe
            20                  25

<210> SEQ ID NO 31
<211> LENGTH: 28
<212> TYPE: PRT
<213> ORGANISM: Homo sapiens

<400> SEQUENCE: 31

Gly Ile Phe Phe Phe Val Ser Tyr Ile Ile Ile Ser Phe Leu Val Val
 1               5                  10                  15

Val Asn Met Tyr Ile Ala Val Ile Leu Glu Asn Phe
            20                  25
```

```
<210> SEQ ID NO 32
<211> LENGTH: 28
<212> TYPE: PRT
<213> ORGANISM: Homo sapiens

<400> SEQUENCE: 32

Gly Ile Cys Phe Phe Cys Ser Tyr Ile Ile Ile Ser Phe Leu Ile Val
 1               5                  10                  15

Val Asn Met Tyr Ile Ala Ile Ile Leu Glu Asn Phe
            20                  25

<210> SEQ ID NO 33
<211> LENGTH: 28
<212> TYPE: PRT
<213> ORGANISM: Homo sapiens

<400> SEQUENCE: 33

Gly Ile Leu Phe Phe Thr Thr Tyr Ile Ile Ile Ser Phe Leu Ile Val
 1               5                  10                  15

Val Asn Met Tyr Ile Ala Ile Ile Leu Glu Asn Phe
            20                  25

<210> SEQ ID NO 34
<211> LENGTH: 28
<212> TYPE: PRT
<213> ORGANISM: Rattus sp.

<400> SEQUENCE: 34

Gly Ile Cys Phe Phe Cys Ser Tyr Ile Ile Ile Ser Phe Leu Ile Val
 1               5                  10                  15

Val Asn Met Tyr Ile Ala Ile Ile Leu Glu Asn Phe
            20                  25

<210> SEQ ID NO 35
<211> LENGTH: 28
<212> TYPE: PRT
<213> ORGANISM: Rattus sp.

<400> SEQUENCE: 35

Gly Ile Leu Phe Phe Thr Thr Tyr Ile Ile Ile Ser Phe Leu Ile Val
 1               5                  10                  15

Val Asn Met Tyr Ile Ala Ile Ile Leu Glu Asn Phe
            20                  25

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Ile Leu Ala Val Val Ala Met Ala Tyr
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 37

Tyr Ile Leu Ala Val Val Ala Met Ala Tyr
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Ile Leu Ala Val Val Ala Met Ala Tyr
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ile Leu Trp Val Val Ala Met Ala Tyr
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Ile Leu Tyr Val Val Ala Met Ala Tyr
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ile Leu Phe Val Val Ala Met Ala Tyr
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ile Cys Trp Val Val Ala Met Ala Tyr
 1               5                  10

-continued

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ile Cys Tyr Val Val Ala Met Ala Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Ile Cys Phe Val Val Ala Met Ala Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Ile Cys Trp Val Val Ala Met Ala Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Ile Cys Tyr Val Val Ala Met Ala Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Ile Cys Phe Val Val Ala Met Ala Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 48

Trp Ile Cys Tyr Val Val Ala Met Ala Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Ile Cys Phe Val Val Ala Met Ala Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Tyr Ile Cys Trp Val Val Ala Met Ala Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Ile Cys Trp Val Val Ala Met Ala Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Ile Cys Tyr Val Val Ala Met Ala Tyr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Ile Cys Phe Val Val Ala Met Ala Tyr
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Ile Cys Phe Val Val Ala Met Ala Tyr
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Ile Cys Tyr Val Val Ala Met Ala Tyr
 1               5                  10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Trp Ala Val Trp Ala Met Ala Tyr
 1               5                  10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Ile Tyr Ala Val Trp Ala Met Ala Tyr
 1               5                  10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ile Phe Ala Val Trp Ala Met Ala Tyr
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Leu Ile Leu Ala Val Trp Ala Met Ala Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met Tyr Ile Ala Trp Ile Leu Glu Asn Phe
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Tyr Ile Ala Tyr Ile Leu Glu Asn Phe
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Tyr Ile Ala Phe Ile Leu Glu Asn Phe
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Tyr Ile Ala Ile Trp Leu Glu Asn Phe
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Tyr Ile Ala Ile Tyr Leu Glu Asn Phe
1               5                   10
```

```
<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Tyr Ile Ala Ile Phe Leu Glu Asn Phe
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Tyr Ile Ala Cys Ile Leu Glu Asn Phe
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Tyr Ile Ala Ile Cys Leu Glu Asn Phe
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Tyr Ile Ala Trp Trp Leu Glu Asn Phe
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Tyr Ile Ala Tyr Tyr Leu Glu Asn Phe
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 70

Met Tyr Ile Ala Phe Phe Leu Glu Asn Phe
 1               5                  10

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (6)
<223> OTHER INFORMATION: Val or Met
<220> FEATURE:
<221> NAME/KEY: MOD_RES
<222> LOCATION: (7)
<223> OTHER INFORMATION: Leu or Val
<220> FEATURE:
<221> NAME/KEY: MOD_RES
<222> LOCATION: (8)
<223> OTHER INFORMATION: Ile or Val
<220> FEATURE:
<221> NAME/KEY: MOD_RES
<222> LOCATION: (17)
<223> OTHER INFORMATION: Ile or Val

<400> SEQUENCE: 71

Tyr Met Ile Phe Phe Xaa Xaa Xaa Ile Phe Leu Gly Ser Phe Tyr Leu
 1               5                  10                  15

Xaa Asn

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 72

Tyr Met Ile Phe Phe Met Leu Val Ile Phe Leu Gly Ser Phe Tyr Leu
 1               5                  10                  15

Val Asn Trp Ile Leu Ala Val Val Ala Met Ala Tyr
                 20                  25

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctcatcaatc tgatctgctg ggtggtggcc atggcgtac                            39

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cctcatcaat tggatctgct gggtggtggc catggcgtac                           40

```
<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cctcatcaat ctgatctgct gggtggtggc catggcatat g                          41

<210> SEQ ID NO 76
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gctctttcta cctcatcaat tggatctgct gggtggtggc catggcatat gc              52

<210> SEQ ID NO 77
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cctggtgaac ctgatctgct gggtggtcgc aatggcc                               37

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccttctacct ggtgaactgg atctgctggg                                       30
```

ISOLATED NUCLEIC ACIDS FOR MUTANT MAMMALIAN NAV 1 PROTEINS

CROSS-REFERENCE TO RELATED APPLICATIONS

This application is a continuation in part of copending U.S. Ser. No. 10/608,584 filed Jun. 26, 2003, the disclosure of which is hereby incorporated by reference.

STATEMENT REGARDING FEDERALLY SPONSORED RESEARCH OR DEVELOPMENT

This invention was made under grant number 5RO1HL6607602 from the National Heart, Lung and Blood Institute. The government may have certain rights in the invention.

FIELD OF THE INVENTION

The invention relates to a method for screening compounds for use as anti-arrhythmic agents. The method employs a cell line that expresses a mutant sodium channel protein.

BACKGROUND OF THE INVENTION

Mammalian voltage-gated sodium channels are pore-forming membrane proteins responsible for the initiation and propagation of action potentials in excitable membranes in nerve, skeletal muscle and heart cells. The controlled gating of sodium channels in response to membrane depolarizations is necessary for normal electrical signaling and establishing of intercellular communication. Voltage-gated Na+ ion channels consist of one large α-subunit (about 200 kDa) and one or two smaller β-subunits. The α-subunits are designated "Nav" (Na for sodium channel and v for voltage-gated), followed by a numbering system for the particular isoform. The Na+ channel α-subunit isoforms contain four homologous repeated domains (D1-D4) each with six transmembrane segments (S1-S6). The α-subunit protein alone forms a functional channel when expressed in mammalian expression systems. The four repeated domains are hypothesized to assemble as a pseudotetrameric structure with the permeation pathway situated at the center. FIG. 1 is a cartoon depicting one conceptualization of how the Nav protein arranges itself with respect to the membrane. The cartoon is not accurate; it is an expanded model that does not attempt to depict how the four S6 segments come together to form the sodium channel, but it facilitates an understanding of how the proteins might align with respect to the inside and outside of the excitable membrane. In fact, recent studies suggest that four S6 C-termini may jointly close the voltage-gated cation channel at the cytoplasmic side, probably as an inverted teepee structure.

Several pieces of evidence suggest that S6 segments are involved in Na+ channel gating. First, a number of receptors for various therapeutic drugs and neurotoxins such as local anesthetics (LAs), antiarrhythmics, anticonvulsants, antidepressants, pyrethroid insecticides, batrachotoxin (BTX), and veratridine, are situated at the middle of multiple S6 segments. Upon binding, these ligands exert their pharmacological actions on the Na+ channel, presumably in part via their corresponding S6 receptor. In particular, BTX drastically modifies Na+ channel activation, fast inactivation, and slow inactivation, suggesting that its receptor is linked to these gating processes.

The invention herein described arose from a hypothesis that S6 segments may be structurally geared for channel activation by lateral/rotational movement via a flexible gating hinge, a glycine or serine residue located at the middle of the inner Na+ channel S6 segments. This gating hinge could have two different conformations. One is in its relaxed straight α-helical form, which closes the channel at the S6 C-terminal end, and the other is the bendable α-helical form, which may bend outward at a 30° angle and thus splay open the channel at the S6 constricted C-terminus. After channel activation, S6 segments may then form the docking site for the fast-inactivation gate. A putative Na+ channel inactivation gate has been delineated at the intracellular linker between D3 and D4 by West et al. [*Proc. Natl. Acad. Sci. USA* 89:10910-10914 (1992)]. This linker could be situated at the C-termini of S6 segments, where the inactivation gate may plug the open channel while it binds to its docking site. This plugging mechanism has recently been demonstrated in voltage-gated K+ channels [Zhou et al., *Nature* 411:657-661 (2001)]. The foregoing hypothesis is useful because it provides a framework for interpreting the results and making predictions. However, it is important to note that the invention is based on the results, not the hypothesis, and the hypothesis should not be viewed as a limitation on the claimed invention.

There is very close homology among the S6 segments of mammalian Nav proteins so far identified. This homology extends both through species and through isoforms of the Nav protein. As can be seen in the comparison below, the few variations that exist among the amino acids in the amino terminal portion of the S6 segments are very conservative replacements, and the carboxy terminal II amino acids of the S6 segments of all four domains are identical for rats and humans for both of the muscle sodium channel proteins Nav1.4 and Nav1.5:

```
                    D1S6
                            1     6     11    16    21    26
            human   Nav1.1  YMIFF VLVIF LGSFY LINLI LAVVA MAY  (SEQ ID NO.: 1)

Nav1.2  YMIFF VLVIF LGSFY LINLI LAVVA MAY  (SEQ ID NO.: 2)

Nav1.3  YMIFF VLVIF LGSFY LINLI LAVVA MAY  (SEQ ID NO.: 3)

Nav1.4  YMIFF VVIIF LGSFY LINLI LAVVA MAY  (SEQ ID NO.: 4)

Nav1.5  YMIFF MLVIF LGSFY LVNLI LAVVA MAY  (SEQ ID NO.: 5)

Nav1.8  YMIFF vVvIF LGSFY LVNLI LAVVA MAY  (SEQ ID NO.: 6)

Nav1.9  YMIFF VVVIF LGSFY LINLI LAVVA MAY  (SEQ ID NO.: 7)

rat     Nav1.4  YMIFF VVIIF LGSFY LINLI LAVVA MAY  (SEQ ID NO.: 8)

Nav1.5  YMIFF MLVIF LGSFY LVNLI LAVVA MAY  (SEQ ID NO.: 9)
```

```
           Nav1.6  YMIFF MLVIF VGSFY PVNLI LAVVA MAY   (SEQ ID NO.: 10)

Nav1.7  YMVFF VVVIF LGSFY LVNLI LAVVA MAY   (SEQ ID NO.: 11)

Nav1.8  YMVFF MLVIF LGSFY LVNLI LAVVA MAY   (SEQ ID NO.: 12)

D2S6
                    1     6     11    16    21    26
human      Nav1.1  CLTVF MMVMV IGNLV VLNLF LALLL SSF   (SEQ ID NO.: 13)

Nav1.2  CLTVF MMVMV IGNLV VLNLF LALLL SSF   (SEQ ID NO.: 14)

Nav1.3  CLIVF MLVMV IGNLV VLNLF LALLL SSF   (SEQ ID NO.: 15)

Nav1.5  CLLVF LLVMV IGNLV VLNLF LALLL SSF   (SEQ ID NO.: 16)

rat        Nav1.4  CLTVF LMVMV IGNLV VLNLF LALLL SSF   (SEQ ID NO.: 17)

Nav1.5  CLLVF LLVMV IGNLV VLNLF LALLL SSF   (SEQ ID NO.: 18)

D3S6
                    1     6     11    16    21    26
human      Nav1.1  MYLYF VIFII FGSFF TLNLF IGVII DNF   (SEQ ID NO.: 19)

Nav1.2  MYLYF VIFII FGSFF TLNLF IGVII DNF   (SEQ ID NO.: 20)

Nav1.3  MYLYF VIFII FGSFF TLNLF IGVII DNF   (SEQ ID NO.: 21)

Nav1.4  MYLYF VIFII FGSFF TLNLF IGVII DNF   (SEQ ID NO.: 22)

Nav1.5  MYIYF VIFII FGSFF TLNLF IGVII DNF   (SEQ ID NO.: 23)

Nav1.8  MYLYF VIFII GGSFF TLNLF VGVII DNF   (SEQ ID NO.: 24)

rat        Nav1.4  MYLYF VIFII FGSFF TLNLF IGVII DNF   (SEQ ID NO.: 25)

Nav1.5  MYIYF VVFII FGSFF TLNLF IGVII DNF   (SEQ ID NO.: 26)

Nav1.7  MYLYF VVFII FGSFF TLNLF IGVII DNF   (SEQ ID NO.: 27)

Nav1.8  MYIYF VVFII FGGFF TLNLF VGVII DNF   (SEQ ID NO.: 28)

D4S6
                    1     6     11    16    21    26
human      Nav1.1  GIFFF VSYII ISFLV VVNMY IAVIL ENF   (SEQ ID NO.: 29)

Nav1.2  GIFFF VSYII ISFLV VVNMY IAVIL ENF   (SEQ ID NO.: 30)

Nav1.3  GIFFF VSYII ISFLV VVNMY IAVIL ENF   (SEQ ID NO.: 31)

Nav1.4  GICFF CSYII ISFLI VVNMY IAIIL ENF   (SEQ ID NO.: 32)

Nav1.5  GILFF TTYII ISFLI VVNMY IAIIL ENF   (SEQ ID NO.: 33)

rat        Nav1.4  GICFF CSYII ISFLI VVNMY IAIIL ENF   (SEQ ID NO.: 34)

Nav1.5  GILFF TTYII ISFLI VVNMY IAIIL ENF   (SEQ ID NO.: 35)
```

Except for a single I→V change at position 7 of D3S6, the rat and human Nav1.4 and Nav1.5 sequences are identical for all four S6 segments. Because of the very high degree of conservation (in fact identity) of the 11 'amino acids' at the carboxy termini of the S6 segments, the person of skill in the art expects that substitution in this region will have the same effect on sodium channel function across mammalian species and across isoforms of the Nav1 protein.

The numbering shown in the charts above is the standard numbering used to identify the 28 amino acids in the S6 segments by their position within that segment. A separate system of numbering that may be applied to those same amino acids derives from their position within the sequence of the whole protein. Because the amino acid sequences of members of the Nav family of proteins vary widely outside the transmembrane regions, the protein sequence residue numbers assigned to the corresponding amino acids in the S6 segments differs among species and among sodium channel protein isoforms within species. Thus, the leucine identified as residue 19 in segment 6 in domain 1 (D1S6) is L407 in human Nav1.5, L408 in rat Nav1.5, L441 in human Nav1.4 and L435 in rat Nav1.4. Similarly, the isoleucine identified as residue 23 in segment 6 in domain 4 (D4S6) is I1770 in human Nav1.5, I1771 in rat Nav1.5, I1581 in human Nav1.4 and I1589 in rat Nav1.4. Unless otherwise noted, amino acids will be identified hereinafter, when referring to the whole protein, according to their position in rNav1.4. Thus A438 refers to the alanine that occurs at position 438 in rNav1.4. The invention, however, is not intended to be limited to polypeptides having sequences derived from the rat; rather, corresponding mammalian sequences, including human are encompassed by the invention.

SUMMARY OF THE INVENTION

In one aspect the invention relates to a method or screen for assessing the potential of a compound to treat a pathological condition, such as arrhythmia, which is manifested by an increased late sodium current in a heart. The method comprises:
(a) providing a recombinant cell that expresses a mutant Nav 1 sodium channel protein;
(b) measuring a first plateau current in the cell;
(c) exposing the cell to a test compound;
(d) measuring a second plateau current in the cell; and
(e) comparing the first and second currents. A lower second current indicates that the test compound is a potential antiarrhythmic agent. The mutant sodium channel protein has an amino acid sequence in which one or more amino acids among the ten amino acids occurring at the carboxy end of the S6 segments of D1, D2, D3 or D4 domains of mammalian Nav1 differs from the amino acid in wild-type Nav1 by substitution with tryptophan, phenylalanine, tyrosine or cysteine. Mammalian Nav 1 proteins encompassed by the present invention encompass mammalian Nav1.1-Nav 1.9.

In another embodiment, the mutant sodium channel protein has an amino acid sequence in which one or more amino acids among the ten amino acids occurring at the carboxy end of the S6 segments of D1, D2, D3 or D4 domains of mammalian Nav1.4 or Nav 1.5 differs from the amino acid in wild-type Nav1 by substitution with tryptophan, phenylalanine, tyrosine or cysteine.

In another embodiment, the mutant sodium channel protein has an amino acid sequence in which at least one of amino acids 19, 21 and 22 of the S6 segment of D1 and amino acids 23 and 24 of the S6 segment of the D4 domain of mammalian Nav1 differs from the amino acid in wild-type Nav1 by substitution with tryptophan, phenylalanine, tyrosine or cysteine.

In another embodiment, the mutant sodium channel protein has an amino acid sequence in which at least one of amino acids 19, 21 and 22 of the S6 segment of D1 and amino acids 23 and 24 of the S6 segment of the D4 domain of mammalian Nav1.4 or Nav1.5 differs from the amino acid in wild-type Nav1.4 or Nav1.5 by substitution with tryptophan, phenylalanine, tyrosine or cysteine.

In another embodiment, the mutant sodium channel protein has an amino acid sequence in which at least one of amino acids L435, L437, A438, I1589 and I1590 of wild-type rNav1.4 is replaced by tryptophan, phenylalanine or tyrosine. L437 of rNav1.4 may be replaced by cysteine, in addition to tryptophan, phenylalanine or tyrosine.

In another aspect, the invention relates to an isolated nucleic acid comprising a nucleotide sequence that codes for a mutant mammalian Nav 1 protein. The mutant protein has a sequence as described above.

In another aspect, the invention relates to a cell transfected with a nucleic acid that encodes a mutant mammalian Nav1 protein. The mutant protein has a sequence as described above.

In another aspect, the invention relates to a functional recombinant sodium channel protein containing an amino acid sequence chosen from:

```
WILAVVAMAY         SEQ ID NO.: 36
YILAVVAMAY         SEQ ID NO.: 37
FILAVVAMAY         SEQ ID NO.: 38
```
-continued
```
LILWVVAMAY         SEQ ID NO.: 39
LILYVVAMAY         SEQ ID NO.: 40
LILFVVAMAY         SEQ ID NO.: 41
LICWVVAMAY         SEQ ID NO.: 42
LICYVVAMAY         SEQ ID NO.: 43
LICFVVAMAY         SEQ ID NO.: 44
WICWVVAMAY         SEQ ID NO.: 45
YICYVVAMAY         SEQ ID NO.: 46
FICFVVAMAY         SEQ ID NO.: 47
WICYVVAMAY         SEQ ID NO.: 48
WICFVVAMAY         SEQ ID NO.: 49
YICWVVAMAY         SEQ ID NO.: 50
FICWVVAMAY         SEQ ID NO.: 51
YICYVVAMAY         SEQ ID NO.: 52
FICFVVAMAY         SEQ ID NO.: 53
YICFVVAMAY         SEQ ID NO.: 54
FICYVVAMAY         SEQ ID NO.: 55
LIWAVWAMAY         SEQ ID NO.: 56
LIYAVWAMAY         SEQ ID NO.: 57
LIFAVWAMAY         SEQ ID NO.: 58
LILAVWAMAY         SEQ ID NO.: 59
MYIAWILENF         SEQ ID NO.: 60
MYIAYILENF         SEQ ID NO.: 61
MYIAFILENF         SEQ ID NO.: 62
MYIAIWLENF         SEQ ID NO.: 63
MYIAIYLENF         SEQ ID NO.: 64
MYIAIFLENF         SEQ ID NO.: 65
MYIACILENF         SEQ ID NO.: 66
MYIAICLENF         SEQ ID NO.: 67
MYIAWWLENF         SEQ ID NO.: 68
MYIAYYLENF         SEQ ID NO.: 69
MYIAFFLENF         SEQ ID NO.: 70
```

In another aspect, the invention relates to a functional recombinant sodium channel protein containing two sequences of amino acids. The first amino acid sequence is chosen from: WILAVVAMAY (SEQ ID NO.: 36); LILWVVAMAY (SEQ ID NO.: 39); LICWVVAMAY (SEQ ID NO.: 42); WICWVVAMAY (SEQ ID NO.: 45), and LILAVWAMAY (SEQ ID NO.: 59). The second amino acid sequence chosen from: MYIAWILENF (SEQ ID NO.: 60);

MYIAIWLENF (SEQ ID NO.: 63); MYIACILENF (SEQ ID NO.: 66); MYIAICLENF (SEQ ID NO.: 67), and MYIAW-WLENF (SEQ ID NO.: 68).

BRIEF DESCRIPTION OF THE DRAWINGS

FIGS. 2A-C illustrates the activation of wild-type Nav 1.4 (A) and rNav 1.4-A438W (B) co-expressed with β1. In 2C normalized conductance ($g_m$) is plotted against pulse voltage for wild type (○) and rNav 1.4-A438W (●)

FIGS. 5A-C shows the steady-state inactivation of wild-type (A) and rNav1.4-A438W (B) coexpressed with β1. Normalized Na$^+$ current availability (h∞) of wild-type (○) and rNav1.4-A438W (●) were plotted as a function of the 100-ms conditioning pulse voltage (C).

DETAILED DESCRIPTION OF THE INVENTION

Figure 1:
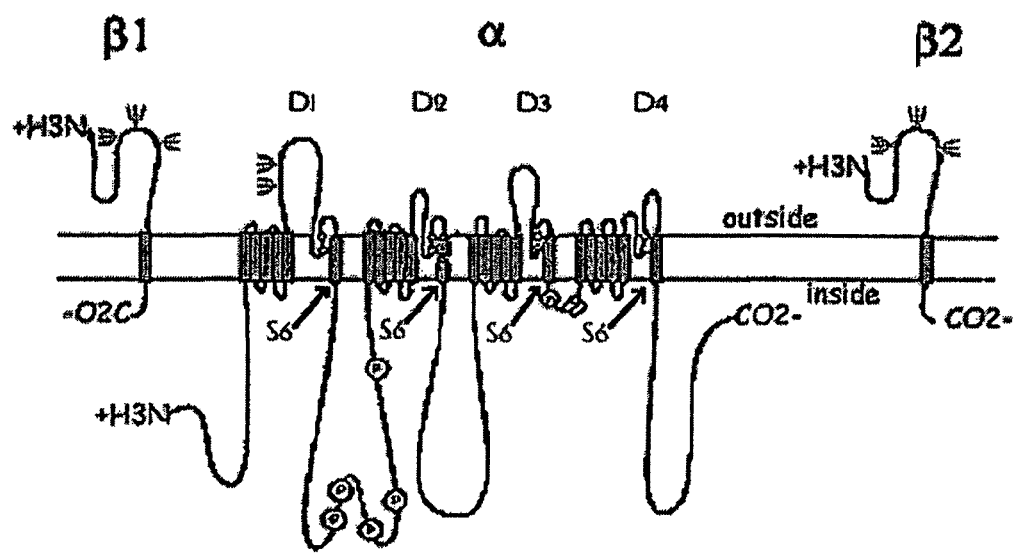
FIG. 1 is a schematic representation of a Nav 1. Na$^+$ channel protein in a cell membrane.

All patents, applications, publications and other references cited herein are hereby incorporated by reference in their entirety into the present application.

The first aspect of the invention relates to a screen for assessing the potential of a compound to treat a pathological condition, such as arrhythmia, which is manifested by an increased late sodium current in a heart. The method comprises:
(a) providing a cell that expresses a recombinant mutant Nav1 sodium channel protein;
(b) measuring a first plateau current in the cell;
(c) exposing the cell to a test compound;
(d) measuring a second plateau current in the cell; and
(e) comparing the first and second currents. A lower second current indicates that the test compound is a potential antiarrhythmic agent. The mutant sodium channel protein has an amino acid sequence in which one or more amino acids among the ten amino acids occurring at the carboxy end of the S6 segments of D1, D2, D3 or D4 domains of a mammalian Nav1 differs from the amino acid in wild-type Nav1.4 or by substitution with tryptophan, phenylalanine, tyrosine or cysteine. In a preferred embodiment, the mutant sodium channel protein has an amino acid sequence in which at least one amino acid chosen from amino acids 19, 21 and 22 of the S6 segment of D1 and amino acids 23 and 24 of the S6 segment of the D4 domain of a mammalian Nav1 is the amino acid that is replaced. These amino acids correspond to amino acids L435, L437, A438, I1589 and I1590 of wild-type rNav1.4. The wild-type amino acids may be replaced by tryptophan, phenylalanine or tyrosine, all of which are neutral, hydrophobic and bulky—the important common features for impairing the so-called "fast inactivation" of the sodium channel. Certain of the wild-type amino acids may also be replaced by cysteine. Cysteine produces a similar impairment of fast inactivation, but appears to do so by an indirect route, whereby it achieves effective bulkiness (and hydrophobicity) through reaction of the sulfhydryl with physiologically accessible nucleophiles. The experiments described below were carried out with tryptophan and cysteine.

The remainder of the Nav protein—outside the S6 segments—is optimally the sequence of a Nav1 sodium channel protein, for example, Nav 1.1, Nav 1.2, Nav 1.3, Nav 1.4, Nav 1.5, Nav 1.6, Nav 1.7, Nav 1.8 or Nav 1.9. Nav1.4 and Nav1.5 are the two isoforms of the Nav protein that are found in skeletal and heart muscle; the remaining isoforms have been primarily identified in the CNS and neuronal structures. In one embodiment, a leucine corresponding to L437 of rNav1.4 is replaced with cysteine, and one or both of a leucine and an alanine corresponding to L435 and A438 respectively are replaced with tryptophan. In other embodiments, alanine corresponding to A438 and an isoleucine corresponding to I1589 are replaced, preferably by tryptophan. Preferred sequences of the residues 19-28 of the S6 segment are:

| | |
|---|---|
| WILAVVAMAY | SEQ ID NO.: 36 |
| YILAVVAMAY | SEQ ID NO.: 37 |
| FILAVVAMAY | SEQ ID NO.: 38 |
| LILWVVAMAY | SEQ ID NO.: 39 |
| LILYVVAMAY | SEQ ID NO.: 40 |
| LILFVVAMAY | SEQ ID NO.: 41 |
| LICWVVAMAY | SEQ ID NO.: 42 |
| LICYVVAMAY | SEQ ID NO.: 43 |
| LICFVVAMAY | SEQ ID NO.: 44 |
| WICWVVAMAY | SEQ ID NO.: 45 |
| YICYVVAMAY | SEQ ID NO.: 46 |
| FICFVVAMAY | SEQ ID NO.: 47 |
| WICYVVAMAY | SEQ ID NO.: 48 |
| WICFVVAMAY | SEQ ID NO.: 49 |
| YICWVVAMAY | SEQ ID NO.: 50 |
| FICWVVAMAY | SEQ ID NO.: 51 |
| YICYVVAMAY | SEQ ID NO.: 52 |
| FICFVVAMAY | SEQ ID NO.: 53 |
| YICFVVAMAY | SEQ ID NO.: 54 |
| FICYVVAMAY | SEQ ID NO.: 55 |
| LIWAVWAMAY | SEQ ID NO.: 56 |
| LIYAVWAMAY | SEQ ID NO.: 57 |
| LIFAVWAMAY | SEQ ID NO.: 58 |
| LILAVWAMAY | SEQ ID NO.: 59 |

-continued

| | |
|---|---|
| MYIAWILENF | SEQ ID NO.: 60 |
| MYIAYILENF | SEQ ID NO.: 61 |
| MYIAFILENF | SEQ ID NO.: 62 |
| MYIAIWLENF | SEQ ID NO.: 63 |
| MYIAIYLENF | SEQ ID NO.: 64 |
| MYIAIFLENF | SEQ ID NO.: 65 |
| MYIACILENF | SEQ ID NO.: 66 |
| MYIAICLENF | SEQ ID NO.: 67 |
| MYIAWWLENF | SEQ ID NO.: 68 |
| MYIAYYLENF | SEQ ID NO.: 69 |
| MYIAFFLENF | SEQ ID NO.: 70 |

The resultant protein may also contain a second amino acid sequence, YMIFFX$^a$X$^b$X$^c$IFLGSFYLX$^d$N (SEQ ID NO. 71), amino-terminal to the foregoing amino acid sequence. In the second sequence, $X^a$ is V or M; $X^b$ is L or V; and $X^c$ and $X^d$ are independently I or V. These variable residues account for the variants thus far observed in S6 residues 1-18 of mammalian Nav proteins. For example, one S6 sequence according to the invention would be YMIFFMLVIFLGSFYLVNWILAVVAMAY (SEQ ID NO. 72).

As will be evident, functional recombinant sodium channel proteins may contain multiple sequences of amino acids altered in the S6 segments of different domains. In preferred multiple-sequence embodiments, a first amino acid sequence may be chosen from: WILAVVAMAY (SEQ ID NO. 36); LILWVVAMAY (SEQ ID NO. 37); LICWVVAMAY (SEQ ID NO. 42); WICWVVAMAY (SEQ ID NO. 45), and LILAVWAMAY (SEQ ID NO. 59), and a second amino acid sequence chosen from: MYIAWILENF (SEQ ID NO. 60); MYIAIWLENF (SEQ ID NO. 63); MYIACILENF (SEQ ID NO. 66); MYIAICLENF (SEQ ID NO. 67), and MYIAWWLENF (SEQ ID NO. 68). For obvious reasons, the two S6 sequences will not commonly be adjacent each other in primary sequence. In fact, in preferred embodiments, the sequences will be separated by at least 400 amino acid residues, and, when the sequences reflect S6 segments in domains 1 and 4, they will be separated by at least 1000 residues.

In another aspect, the invention relates to a cell comprising a recombinant nucleic acid that encodes a mutant mammalian Nav1 protein. The mutant protein has a sequence as described above, and the cell expresses sodium channels that exhibit a plateau current of greater than 1 nanoamp. The process for transfecting a cell with an appropriate nucleic acid is well known in the art. The particular cell chosen for transfection was the human embryonic kidney (HEK293t) cell. Chinese hamster ovary cells are also well suited for this purpose. The person of skill will be aware of cell lines that become known in the art for their ability to express proteins of the size (200 kDa) of the Nav protein, and these will be appropriate for transfection with the nucleic acids of the invention. Any eukaryotic cells which support stable replication of plasmids containing nucleic acids encoding the mutant sodium channels described above may be used in practicing the invention. Non-limiting examples of host cells for use in the present invention include HEK 293 cells (American Type Culture Collection, Manassas, Va. (ATCC Cat. No. CRL-1573), CV-1/EBNA-1 cells (ATCC Cat. No. CRL 10478), HeLa cells, D98/raji cells, 293EBNA (Invitrogen, Cat. No.

R62007), CV-I cells (ATCC Cat. No. CCL 70) and 143B cells (ATCC Cat, No. CRL-8303). In addition, primary cultures of eukaryotic cells may be isolated from their tissue of origin and transfected with the appropriate expression vector.

One of the advantages of the substitutions of the present invention is that, unlike all previously reported mutants of the Nav protein, substitution with W, F, Y or C in the carboxy terminal ten residues of S6, when expressed at a useful level, results in a cell line that is viable (the leakage is not lethal to the cell), while at the same time the cells exhibit a large enough sodium channel current to make measurement reliable.

In practicing the present invention, many conventional techniques in molecular biology, microbiology, and recombinant DNA are used. Such techniques are well known and are explained in, for example, Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins, eds.); *Transcription and Translation*, 1984 (Hames and Higgins, eds.); *Animal Cell Culture*, 1986 (R.I. Freshney ed.); *Immobilized Cells and Enzymes*, 1986, (IRL Press); Perbas, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology Vol. 154 and Vol. 155* (Wu and Grossman, and Wu, eds., respectively); *Current Protocols in Molecular Biology*, John Wiley & Sons, Inc. (1994), and all more current editions of these publications. Throughout this application, various references are referred to within parentheses or square brackets. The disclosures of these publications in their entireties are hereby incorporated by reference as if written herein.

In the description that follows, certain conventions will be followed as regards the usage of terminology. The term "expression" refers to the transcription and translation of a structural gene (coding sequence) so that a sodium channel protein (i.e. expression product) having biological activity is synthesized. It is understood that post-translational modifications may remove portions of the polypeptide that are not essential and that glycosylation and other post-translational modifications may also occur. The term "transfection," as used herein, refers to the uptake, incorporation and expression of exogenous DNA into a host cell by any means, and includes, without limitation, transfection of plasmids, episomes and other circular DNA forms. The expression vector may be introduced into host cells via any one of a number of techniques including but not limited to viral infection, transformation, transfection, lipofection or other cationic lipid based transfection, calcium phosphate co-precipitation, gene gun transfection, and electroporation. These techniques are well known to persons of skill in the art.

The term "sodium channel protein" refers to any protein that provides a functional sodium channel in an excitable membrane. Known sodium channel proteins are the isoforms of the Nav family: Nav 1.1 through Nav 1.9, Nav 2.1 through Nav2.3 and Nav 3.1. [See Goldin *Ann. N.Y. Acad. Sci* 868: 38-50 (1999)]. For the present invention, type I Nav proteins (referred hereinafter as Nav 1 or Nav 1.x) are preferred, with Nav1.4 and Nav1.5 being more preferred. The term "mutant sodium channel protein" or "recombinant sodium channel protein" refers to a recombinant protein having the sequence of a Nav 1 protein, that is, Nav1.1 through Nav 1.9, in which from one to ten amino acids differ from the wild-type. The person of skill will of course recognize that in proteins of 2000 amino acids, such as those of the Nav family, there can be innumerable deletions, insertions and substitutions that do not affect the function of the protein in any measurable way. Proteins having >90% homology to a protein in the Nav family but containing deletions, insertions and substitutions that do not affect their function in providing a sodium channel are to be considered equivalents of the claimed mutants. Furthermore, because the genetic code is degenerate, more than one codon may be used to encode a particular amino acid, and therefore, the amino acid sequence can be encoded by any set of similar DNA oligonucleotides. With respect to nucleotides, therefore, the invention encompasses all the DNA sequences containing alternative codons, which code for the eventual translation of the identical amino acid.

The term "plateau current" refers to the current measured in a single cell 5 ms after activation by a sufficient voltage pulse to open the channel. For cells expressing wild-type Nav 1.4 and 1.5 the pulse is $-60\pm10$ mV and the plateau current is below 1 nA. For cells expressing mutant Nav1.4 and 1.5 according to the invention, the pulse can be somewhat higher (e.g. $-70\pm10$ mV) and the plateau current is above 1 nA.

The utility of the mutant Nav test system has been demonstrated with flecainide. Flecainide is one of several orally active class Ic antiarrhythmic drugs. The primary target of flecainide is the cardiac $Na^+$ channel, which is responsible for the upstroke of cardiac action potentials. Recently, flecainide has been found effective for patients with the Long QT syndrome [Windle, et al., *Ann. Noninvasive Electrocardiol.* 6(2): 153-158 (2001)]. The state-dependent binding of flecainide with wild type and an exemplary inactivation-deficient sodium channel of the invention (rNav1.4-L435W/L437C/A438W) were compared in the HEK293t expression system. Unlike the inactivation-deficient cardiac Nav1.5 IFM/QQQ mutant of Grant et al. [*Biophysical J.* 79:3019-3035 (2000)], the channel of the invention expressed well, which is evident from the large sodium currents (>1 nanoamp following $-50$ mV stimulation), and we demonstrate below that flecainide binds rapidly and preferentially with the open state but minimally with the resting state. This provides the basis for the first truly useful, high-throughput screen for agents that may be used to treat various pathological conditions that manifest an increase in persistent late sodium currents in the heart. Such agents include antiarrhythmic agents. To screen for such agents, one follows the procedure described in the experiments described below, and one simply replaces flecainide by a test agent.

The invention began from the hypothesis that an amino acid having a bulky hydrophobic side chain, would disrupt or alter channel function because of its large size. The disruption or alteration would occur if a large hydrophobic amino acid were substituted for an amino acid that contacts or directly interacts with other parts of the channel protein. In addition, it was possible that the effects of several residues on the fast inactivation gating would be additive after multiple substitutions. The experiments below employed tryptophan (W) and cysteine (C) as the prototypic bulky, hydrophobic amino acids.

In practicing the method of the invention, a mammalian mutant Nav 1 sodium channel protein is expressed in an appropriate cell. The cell expressing the sodium channel of the invention is contacted with a compound to determine whether the compound has potential utility as an anti-arrhythmic agent.

Isolated nucleic acids comprising a nucleotide sequence that codes for a mutant mammalian Nav 1 protein according to the invention may be obtained by methods known to one of skill in the art. Site-directed mutagenesis of DNA from appropriate cells, for example, heart and smooth muscle, or cell line cultures of the appropriate species or tissue, is then performed to obtain a nucleic acid encoding mutant sodium channel protein as described above.

Isolation of DNA

DNA encoding a $Na^+$ channel, in accordance with the instant invention, may be obtained by screening reverse transcripts of mRNA or cDNA from appropriate cells or tissues, for example, CNS, skeletal muscle, denervated skeletal muscle, cardiac muscle, uterus, astrocytes or cell line cultures of the appropriate tissues, by screening genomic libraries, or by combinations of these procedures. Screening of mRNA, cDNA or genomic DNA may be carried out with oligonucleotide probes generated from the nucleic acid sequence information of the sodium channel proteins disclosed herein.

An alternative means to isolate the gene encoding a Nav sodium channel protein is to use polymerase chain reaction (PCR) methodology as described in Sambrook et al., *Molecular Cloning: A Laboratory Manual*, second edition, Cold Spring Harbor Laboratory Press, Cold Spring Harbor, N.Y.

Site-directed Mutagenesis

The QUIKCHANGE XL™ site-directed mutagenesis kit (Stratagene, La Jolla, Calif.) was used to create rat skeletal muscle Nav1.4 mutant clones as previously described (Wang and Wang, Biophys. J. 72:1633-1640, 1997; Wang and Malcolm, BioTechniques 26:680-682, 1999). Preliminarily, a wild type rNav 1.4-pcDNA1/Amp clone was generated to serve as the template for mutagenesis. Briefly, a cDNA insert prepared from the wild type rat muscle cDNA Nav 1.4, clone μ1-2, (Genbank accession number M26643) (Trimmer et al., Neuron 3: 33-49, 1989) was cloned into the EcoRI site of a pcDNA1/Amp vector (Invitrogen, Carlsbad, Calif.) to yield the vector rNav 1.4-pcDNA1/Amp. For mutagenesis, two complementary mutant oligonucleotides of 38-42 nucleotides in length (see Table 1) are annealed to the template DNA in separate tubes for 4 cycles of PCR reaction (94° C., 30 sec; 55° C., 1 min, 68° C., 23 min).

TABLE 1

Primers for Site-Directed Mutagenesis

Clones rNav 1.4 437C438W/rNav 1.4 435 W437C438W:

5'-ctcatcaatctgatctgctgggtggtggccatggcgtac-3'
(SEQ ID NO.: 73)

5'-cctcatcaattggatctgctgggtggtggccatggcgtac-3'
(SEQ ID NO.: 74)

Clones hNav 1.4 443C444W/hNav 1.4 441W443C444W

5'-cctcatcaatctgatctgctgggtggtggccatggcatatg-3'
(SEQ ID NO.: 75)

5'-gctctttctacctcatcaattggatctgctgggtggtggccatggca
tatgc-3'
(SEQ ID NO.: 76)

hNav 1.5 409C410W

5'-cctggtgaacctgatctgctgggtggtcgcaatggcc-3'
(SEQ ID NO.: 77)

5'-ccttctacctggtgaactggatctgctggg-3'
(SEQ ID NO.: 78)

The PCR reaction mix contains template DNA (0.4 ng/ul), primer (5 ng/ul), KCl (10 mM), $(NH_4)_2SO_4$ (10 mM), Tris-HCl (pH8.8) (20 mM), $MgSO_4$ (2 mM), TritonX-100 (0.1%), 0.1 mg/ml bovine serum albumin, deoxynucleotides mix (0.4 mM each), pfuTurbo DNA polymerase (0.05 U/ul). The stage 2 PCR reactions follow after mixing the two primer stage 1 reactions into one and perform the following PCR reactions: 94° C., 30 sec, 18 cycles of (94° C., 30 sec, 55° C., 1 min; 68° C., 23 min). The in vitro synthesized DNA is digested with DpnI at 0.2 U/ul at 37° C. for one hour. One μl of the DpnI treated DNA is transformed into XL-Gold ultracompetent cells (Strategene, La Jolla Calif.), plated on Ampicillin (50 ug/ml) LB plates. Bacterial colonies are picked into LB containing Ampicillin at 50 ug/mlDNA. The mutation frequency is 25-100%, that is, you will obtain at least one mutant if you sequence 4 clones.

To minimize the possibility that unique phenotypes are due to unwanted mutations, independent clones of rNav1.4-L435W/L437C/A438W and rNav1.4-L437C/A438W as well as additional homologous L435W/L437C/A438W clones from human isoforms (hNav1.4 and hNav1.5) were created. Preliminary results showed that all of these independent and homologous clones displayed comparable phenotypes to those of rNav1.4 counterparts. DNA sequencing near the mutated site was performed to confirm the mutations.

Transient Transfection

Transfection methods are well known in the art. In one embodiment, human embryonic kidney (HEK293t) cells were grown to ~50% confluence in DMEM (Gibco) containing 10% fetal bovine serum (HyClone, Logan Utah), 1% penicillin and streptomycin solution (Sigma, St. Louis, Mo.), 3 mM taurine, and 25 mM HEPES (Gibco). HEK293t cells were then transfected with cloned $Na^+$ channels, either wild type or mutant, by a calcium phosphate precipitation method in a TI-25 flask (Cannon and Strittmatter, 1993). A reporter plasmid CD8-pih3m and cDNA clone in the pcDNA1/amp vector (Invitrogen, San Diego, Calif.) were prepared in 250 mM $CaCl_2$, added to a test tube containing 0.36 ml of Hanks' balanced salt solution and incubated at 22° C. for 20 min. The DNA solution was then dripped over a cell culture (30-50% confluence) containing 7 ml of DMEM. The transfected cells were trypsinized and replated 15 h later to an appropriate density in 35-mm tissue culture dishes containing 2 ml of fresh DMEM. Transfected cells were maintained at 37° C. in a humidified 5% $CO_2$ incubator, and used after 1-4 days. Transfection-positive cells, which were identified by binding to immunobeads (CD8-Dynabeads, Dynal, Lake Success N.Y.) coated with a monoclonal antibody specific for CD8 antigen, were selected for patch-clamp experiments.

Transfection of wild type rNav1.4-pcDNA1/Amp or mutant clones (5-10 μg) along with β1-pcDNA1/Amp (10-20 μg) and reporter CD8-pih3m (1 μg) generated sufficient sodium channel expression for later current recording.

Measurement of $Na^+$ Current

Whole-cell configuration was used to record $Na^+$ currents according to the method of Hamill et al. [*Pflugers Arch.* 391:85-100 (1981)]. Borosilicate micropipettes (Drummond Scientific Company, Broomall, Pa.) were pulled with a puller (P-87, Sutter Instrument Company, Novato, Calif.) and heat polished. Pipette electrodes contained 100 mM NaF, 30 mM NaCl, 10 mM EGTA, and 10 mM HEPES adjusted to pH 7.2 with CsOH. The pipette electrodes had a tip resistance of 0.5 to 1.0 MΩ. Access resistance was 1-2 MΩ and was further reduced by series resistance compensation. All experiments were performed at room temperature (22-24° C.) under a $Na^+$-containing bath solution with 65 mM NaCl, 85 mM choline Cl, 2 mM $CaCl_2$, and 10 mM HEPES adjusted to pH 7.4 with tetramethylammonium hydroxide. Residual outward currents were evident in some cells at voltages ≧+30 mV;

these currents were present in untransfected cells and were insensitive to tetrodotoxin. These residual currents were not subtracted from the measurements. Whole-cell currents were measured by an AXOPATCH 200B™ (Axon Instruments, Foster City, Calif.) or an EPC-7 (List Electronics, Darmstadt/ Eberstadt, Germany), filtered at 3 kHz, collected, and analyzed with pClamp8 software (Axon Instruments). Leak and capacitance were subtracted by the patch clamp device and further by the leak subtraction protocol (P/−4). Cells were held at −140 mV for functional characterizations. Voltage error was <4 mV after series resistance compensation. An unpaired Student's t test was used to evaluate estimated parameters (mean±SEM or fitted value ±SE of the fit); P values of <0.05 were considered statistically significant.

Gating properties of W substitutions within the C-terminus of D1S6 in Nav1.4 Na$^+$ channels were examined. To characterize the effects of W substitutions, we measured Na$^+$ currents of D1S6 W-substituted mutant channels at various voltages. Each of residues 19 to 28 (the carboxy terminus of S6) was replaced by W.

FIGS. 2A and B show the superimposed current families of Nav1.4 wild type and mutant Nav1.4-A438W (position 22 at D1S6) (B) respectively, cotransfected with β1 subunit. Activation threshold was around −50 mV for wild type and around −60 mV for A438W mutant channels. Families of $Na^+$ currents for wild type (A) and Nav 1.4−A438W mutant (B) were evoked by 5 ms pulses from the holding potential (−140 mV) to voltages ranging from −120 to +50 mV in 10-mV increments. The current traces evoked by a pulse to −50 mV and to +50 mV are labeled. Normalized membrane conductance ($g_m$)(C) was determined from the equation $g_m = I_{Na}/E_m - E_{Na}$), where $I_{Na}$ is the peak current, $E_m$ is the amplitude of the pulse voltage, and $E_{Na}$ is the reversal potential, and plotted against the pulse voltage. Plots were fitted with a Boltzmann function, which yielded the midpoint voltage ($V_{0.5}$) and slope (k) for wild-type (open circle, n=5) of −32.0±0.9 nV and 8.7±0.8 nV, respectively, and −38.8±1.2 mV and 13.1±1.1 mV for rNav 1.5−A438W (closed circles, n=6)(FIG. 2C). The W mutant showed an apparent leftward shift of −6.8±2.1 mV (n=6).

FIG. 3 is a summary of effects of W- and selected C-mutations at C-termini of D1S6 and D4S6 on activation and inactivation gating. In the left panel is a vertical representation of amino acid sequences of D1S6 (top), D4S6 (middle), and double and triple mutants (bottom). All mutants and wild-type $Na^+$ channels were co-transfected with the β1 subunit. Activation Shift: the bar graph shows the differences in voltage for the half-maximal activation ($V_{0.5}$) of the wild-type and mutant $Na^+$ channels. The $V_{0.5}$ values (mean±SEM) were obtained from the Boltzmann fits of normalized conductance versus voltage plots as described above for FIG. 2. Significantly, the estimated reversal potential ($E_{Na}$) remained about the same in these mutants. Bars in gray indicate single C-substitution. Non-expressing mutants are noted with an X. Slope Effect (Activation, Inactivation): this bar graph shows the differences in k values for the wild-type and mutant channels. The k values (mean±SEM) were obtained from Boltzmann fits of I/V plots (activation) and from Boltzmann fits of steady-state inactivation plots (inactivation), as described for FIG. 2 and FIG. 5, respectively. Inactivation Shift: the bar graph shows the differences in voltage for the half-maximal inactivation ($h_{0.5}$) of the wild-type and mutant $Na^+$ channels. The $h_{0.5}$ values (mean±SEM) were obtained as described for FIG. 5. All values were derived from n=4-6, except E1592W with n=3. An asterisk (*) indicates that the value is statistically different from that of the wild type (p<0.05). Except for L435W and I436W, all other D1S6 mutants W displayed a leftward shift. L437W shifted leftward by as much as −22.1±2.0 mV (n=5). The slope factor for each W mutant showed either no significant change or became less steep.

Another noticeable change in gating after A438W substitution was the non-inactivating currents maintained at the end of the pulse (FIG. 2B vs. 2A). To quantify this difference between wild type and mutant channels we measured the amount of the non-inactivating maintained current near the end of 5-ms +50 mV pulse. The wild-type current decayed rapidly and reached its steady-state level within 2-3 ms and 2.9±0.8% (n=5) of currents were maintained under these experimental conditions. In contrast, Nav1.4-A438W mutant showed conspicuous maintained currents under identical conditions. As measured near the 5-ms time, 31.9±4.2% (n=6) of currents were non-inactivating. Thus, a substitution of W at position 22 of D1S6 impairs the $Na^+$ channel fast inactivation significantly (P<0.001).

In FIG. 4, the relative maintained currents in various W- and C- mutations of C-termini of D1S6 and D4S6 are shown, with the relative non-inactivating components of all mutants at D1S6 on the left. Cells were cotransfected with β1 subunit; non-expressing mutants are indicated by an X. The fraction of non-inactivating current was determined as the averaged current amplitude near 5 ms after the +50 mV pulse (e.g., FIG. 2) divided by the peak current. Error bars indicate standard error. Astericks indicate significant differences from the wild-type channels as determined by a t test (p<0.05, n=4−6). Dotted line indicates the value of wild-type. Bars in gray indicate single C-substitution.

The two other W mutants with impaired fast inactivation are L435W (FIG. 4; the fraction of non-inactivating current=0.10±0.02, n=5, P<0.05; position 18) and L437W (0.055±0.017, n=5, P=0.20; position 21).

Using various conditioning pulses from −160 mV to −15 mV, we further characterized the steady-state inactivation of the mutant channels. FIGS. 5A and B show $Na^+$ currents of the wifld type and Nav1.4-A439W mutant, respectively, cotransfected with β1 subunit, evoked by a 5-ms test pulse to +30 mV. Test pulses were preceded by 100 ms conditioning pulses ranging from −160 mV and −15 mV in 5-mV increments. Small non-inactivating inward currents appeared at conditioning voltages ≧−60 mV.

Peak currents were measured, normalized with respect to the peak current at −160 mV and plotted against conditioning voltages. In FIG. 5C, normalized $Na^+$ current availability (h∞) of wild type (open circle, n=5) and rNav1.4-A438W (closed circle, n−5) were plotted as a function of the 100 ms conditioning pulse voltage. The data were fitted with a standard Bolzmann equation. The fitted midpoint($h_{0.5}$) and slope factor (k) for wild-type were −73.4±0.1 mV and 5.0±0.1 mV, respectively, and +89.0±0.3 mV and 6.0±0.2 mV for Nav1.4−A438W, respectively. The shift in the $\Delta V_{0.5}$ is shown in FIG. 3 (top on right side) along with the shift in the slope factor, the Δk value.

The residues from position 19 to 26 in D4S6 were also substituted with tryptophan (FIG. 1; solid bracket). FIGS. 6A and B show the current voltage relationship and steady state inactivation measurement of mutant Nav1.4-I1589W, respectively. In 6A superimposed $Na^+$ current traces were evoked by 5-ms pulses from the holding potential (−140 mV) to voltages ranging from −120 to +50 mV in 10-mV increments. For 6B, superimposed currents were envoked by a 5-ms test pulse to +30 mV preceded by 100-ms conditioning pulses ranging from −160 mV to −15 mV in 5-mV increments.

Normalized $Na^+$ conductance ($g_m$), as shown in FIG. 6C, were derived from A as described above for FIG. 2, plotted against voltage, and fitted with a Boltzmann function. The fitted midpoint voltage ($V_{0.5}$) and slope (k) of the function for wild-type (open circles, n=5) were −32.0±0.9 and 8.7±0.8, respectively, and −19.0±1.0 and 12.6±0.9, respectively for rNav1.4-I1589W (closed circles, n=6). Normalized Na$^+$ current availability (h∞) of wild-type (open down triangle, n=5) and Nav1.4-I1589W (closed down triangle, n=5) were derived from (B) as described for FIG. 5, and plotted as a function of conditioning voltage. Plots were fitted with the Boltzmann function. The midpoint ($h_{0.5}$) and slope factor (k) for wild-type were −73.4±0.1 and 5.0±0.1, respectively, and −66.5±0.2 and 5.7±0.2, respectively, for the Nav1.4-I1589W. Cells were cotransfected with β1 subunit.

Figure 3:
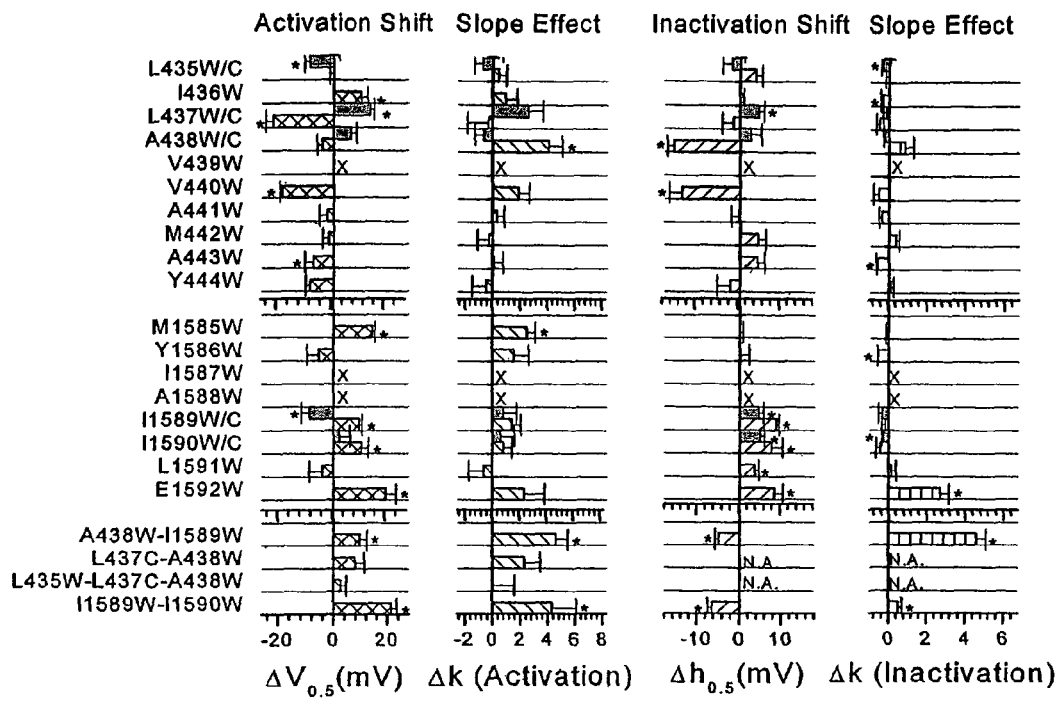
FIG. 3 is a graphic summary of the effects of W- and selected C- mutations at C-termini of D1S6 and D4S6 on activation and inactivation gating.

Again there were significant non-inactivating currents maintained at the end of test pulse for I1589W. The relative amounts of the maintained currents of all mutants at D4S6 are listed in FIG. 4 (middle section) along with D1S6 mutants. The activation of I1589W was shifted rightward by 13.0±1.9 mV (n=6) and the steady state inactivation was shifted rightward by 6.8±0.3 mV (n=5). These changes in gating parameters of all D4S6 mutants are listed in FIG. 3 (middle section). Two W mutant channels (I1589W and I1590W) appeared to have significantly impaired fast inactivation. Two mutants, I1587W and A1588W, expressed Na$^+$ currents below 1 nA in this expression system.

Figure 7:
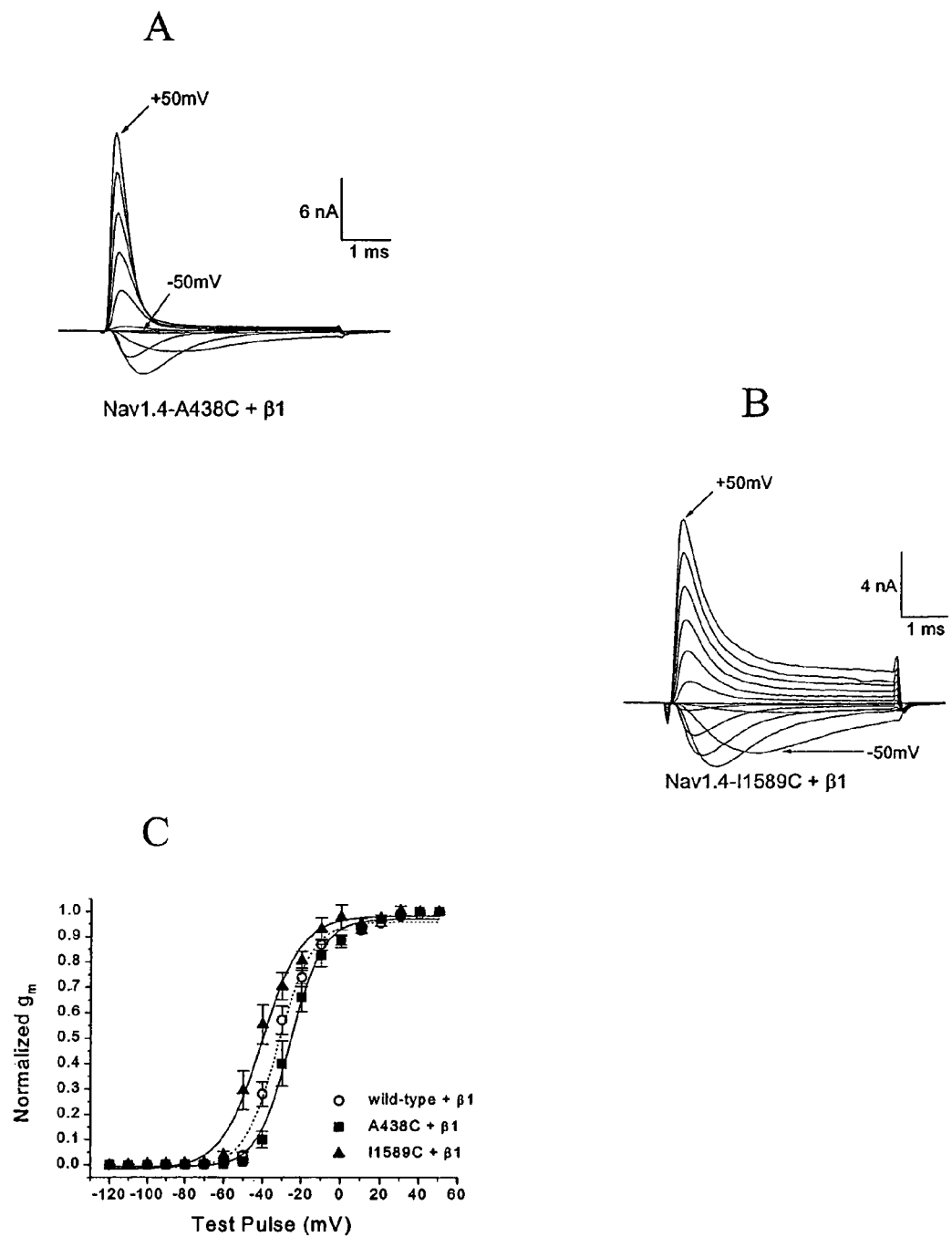
FIGS. 7A-C shows activation of rNav1.4-A438C (A) and rNav1.4-I1589C (B) coexpressed with β1. Normalized membrane conductance ($g_m$) is plotted against the amplitude of the 5-ms voltage step in (C).

There is not a clear relationship between the size of residue in the native amino acid and the degree of the impairment in fast inactivation. FIGS. 7A and B show the current families of A438C and I1589C, respectively. Superimposed Na$^+$ current families of Nav1.4-A438C (7A) and Nav1.4-I1589C (7B) were evoked by 5-ms pulses from holding potential of −140 mV to voltages ranging from −120 to +50 mV in 10-mV increments. In FIG. 7C, normalized membrane conductance ($g_m$) is plotted versus the amplitude of the 5-ms voltage step. $G_m$ was determined as described for FIG. 2 above, plotted against the membrane voltage, and fitted with a Boltzmann function. The fitted midpoint voltage ($V_{0.5}$) and slope (k) of the function for wild-type (open circles, n=5) were −32.0±0.9 and 8.7±0.8, respectively, −25.9±0.7 and 8.3±0.6 for Nav1.4-A438C (closed square, n=5), and −39.9±1.1 and 10.9±0.9 for Nav1.4-I1589C (closed triangle, n=6). Cells were cotransfected with β1 subunit.

Figure 4:
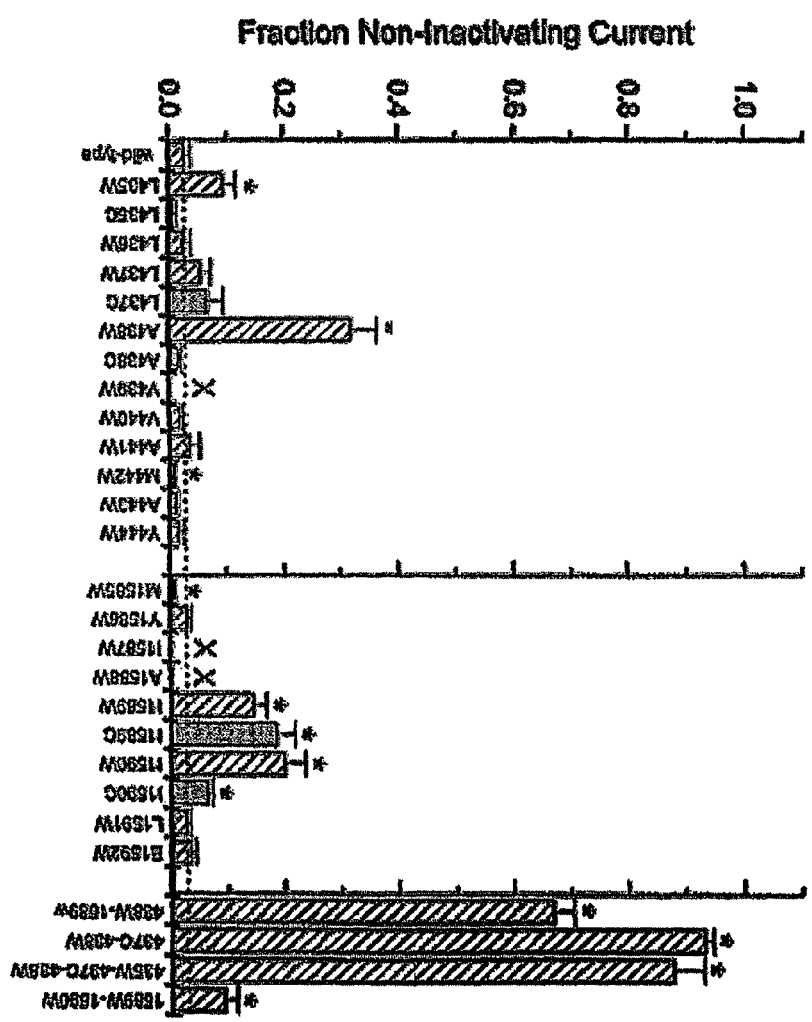
FIG. 4 is a bar graph depicting the relative maintained currents in various W- and C-mutations at C-termini of D1S6 and D4S6. Fraction of non-inactivating current for D1S6 mutants (left), D4S6 (middle), and double and triple mutants (right).
Figure 6:
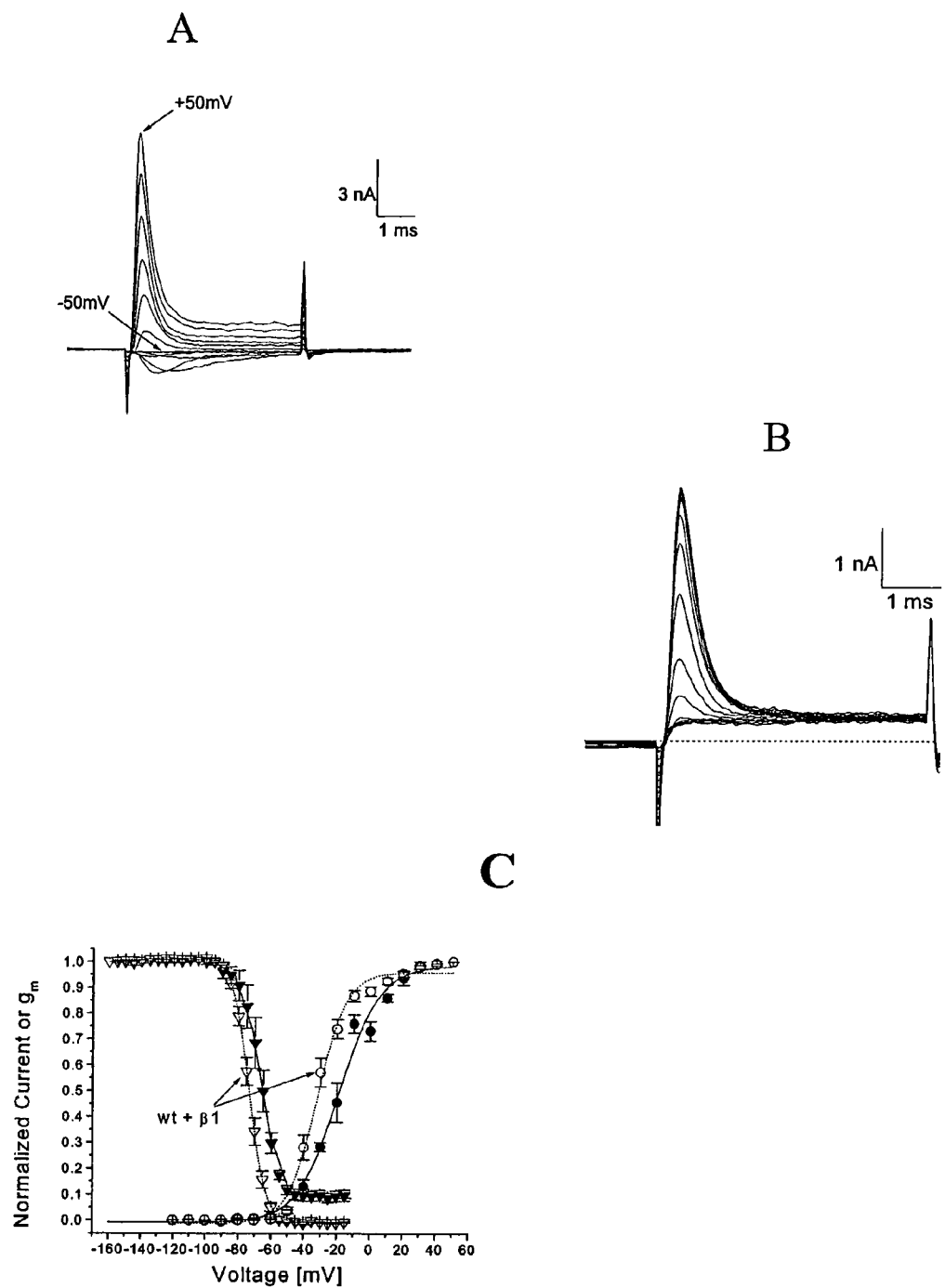
FIGS. 6A-C shows gating properties of rNav1.4-I1589W coexpressed with β1.

A438W and I1590W exhibited significantly impaired fast inactivation but A438C and I1590C do not (FIGS. 2,4). In contrast, I1589C displayed impaired fast inactivation similar to that of I1589W (FIG. 4). This lack of direct correlation in volume suggests that either allosteric effects occur after amino acid substitutions (i.e. the sulfhydryl undergoes reaction with a nearby bulky, hydrophobic nucleophile) or these residues may specifically and directly interact with other parts of channel structure, such as the inactivation gate.

Gating properties of double and triple substitutions of residues within D1S6 and D4S6 were also tested. Selected residues (L435, L437, A438, I1589, I1590) were multiply substituted.

Figure 8:
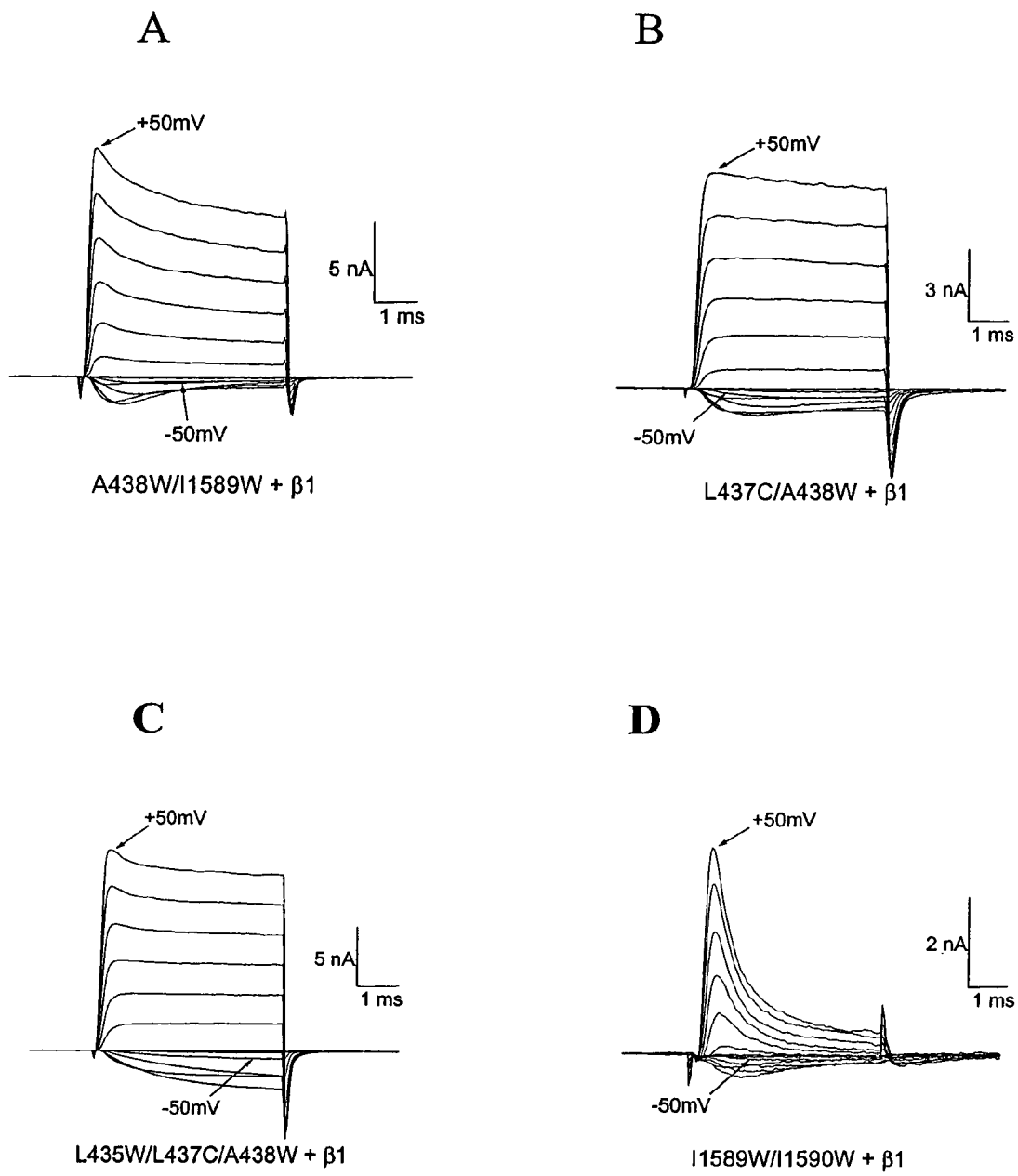
FIGS. 8A-D shows activation gating of double and triple mutants cotransfected with β1: A438W/I1589W (A); L437C/A438W (B); L435W/L437C/A438W (C); I1589W/I1590W (D).

Superimposed Na$^+$ current families were evoked by 5-ms pulses from holding potential of −140 mV to voltages ranging from −120 to +50 mV in 10-mV increments for mutants A438W/I1589W (A), L437C/A438W (B), L435W/L437C/A438W (C) AND I1589W/I1590W (D). FIGS. 8A, B, C and D show the current families of A438W/1589W, L437C/A438W, L435W/L437C/A438W, and I1589W/I1590W, respectively.

Several multiple-substituted mutants expressed a high level of Na$^+$ currents comparable to that of wild type. There were two distinct types of phenotypes from these mutants. One type showed supra-additive effects on the fast inactivation and the other showed sub-additive effects. The results thus demonstrate that it is feasible to create fast-inactivation deficient mutants that express well in a mammalian expression system.

When the fast inactivation was hampered by pronase or by site-directed mutagenesis, slow inactivation gating not only remained functional but also was accelerated considerably. This inverse relationship suggests that the fast inactivation and slow inactivation gating have distinct identities and yet these two gating processes are somehow coupled. To determine whether such inverse relationship holds true in S6 mutants with severely impaired fast inactivation, we therefore measured the slow inactivation gating with a 10-s conditioning prepulse at various voltages.

To induce slow inactivation, we applied conditioning prepulses ranging from −180 mV to 0 mV with a duration of 10 s. After a 100-ms interval at −140 mV, Na$^+$ currents were evoked by the delivery of a +30 mV test pulse. (A) Peak Na$^+$ currents were normalized to the corresponding current obtained with a prepulse to −180 mV and plotted against conditioning prepulse potential. Data were fitted with a Boltzmann function. The fitted $V_{0.5}$ values and k (slope factor) values from the Boltzmann functions were (in mV) −51.1±0.5 and 9.7±0.4, respectively, for wild-type (open circle, n=5); −49.9±0.1 and 5.0±0.1, respectively, for L435W/L437C/A438W (closed circle, n=5); −45.2±0.3 and 5.8±0.2, respectively, for L437C/A438W (closed up triangle, n=5); −45.2±0.3 and 6.8±0.3, respectively, for A438W/I1589W (closed down triangle, n=6); and −50.0±0.9 and 9.5±0.8, respectively, for I1589W/I1590W (closed diamond, n=5). The final steady-state non-inactivated values (in %) were 57.5±0.4 (wild-type), 3.3±0.4 (L435W/L437C/A438W), 12.3±0.6 (L437C/A438W), 11.6±0.8 (A438W/I1589W), and 3.4±1.7 (I1589W/I1590W). All mutants are co-transfected with the β1 subunit. (B) Development of slow inactivation. For the development of slow inactivation, the prepulse duration at +30 mV was varied ranging from 0 to 10s. The peak current at the test pulse of +30 was measured and normalized to the initial peak amplitude without a prepulse, and then plotted against the prepulse duration. The data were fitted by a single-exponential function. The τ values (and final steady-state $Y_0$ values) for wildtype, L435W/L437C/A438W, L437C/A438W, A438W/I1589W, and I1589W/I1590W are 4.8±0.3 s (51.6%), 0.72±0.01 s(3.0%), 0.50±0.01 s (16.6%), 0.64±0.02 s (10.5%), and 0.81±0.02 s (16.6%), respectively.

Figure 9:
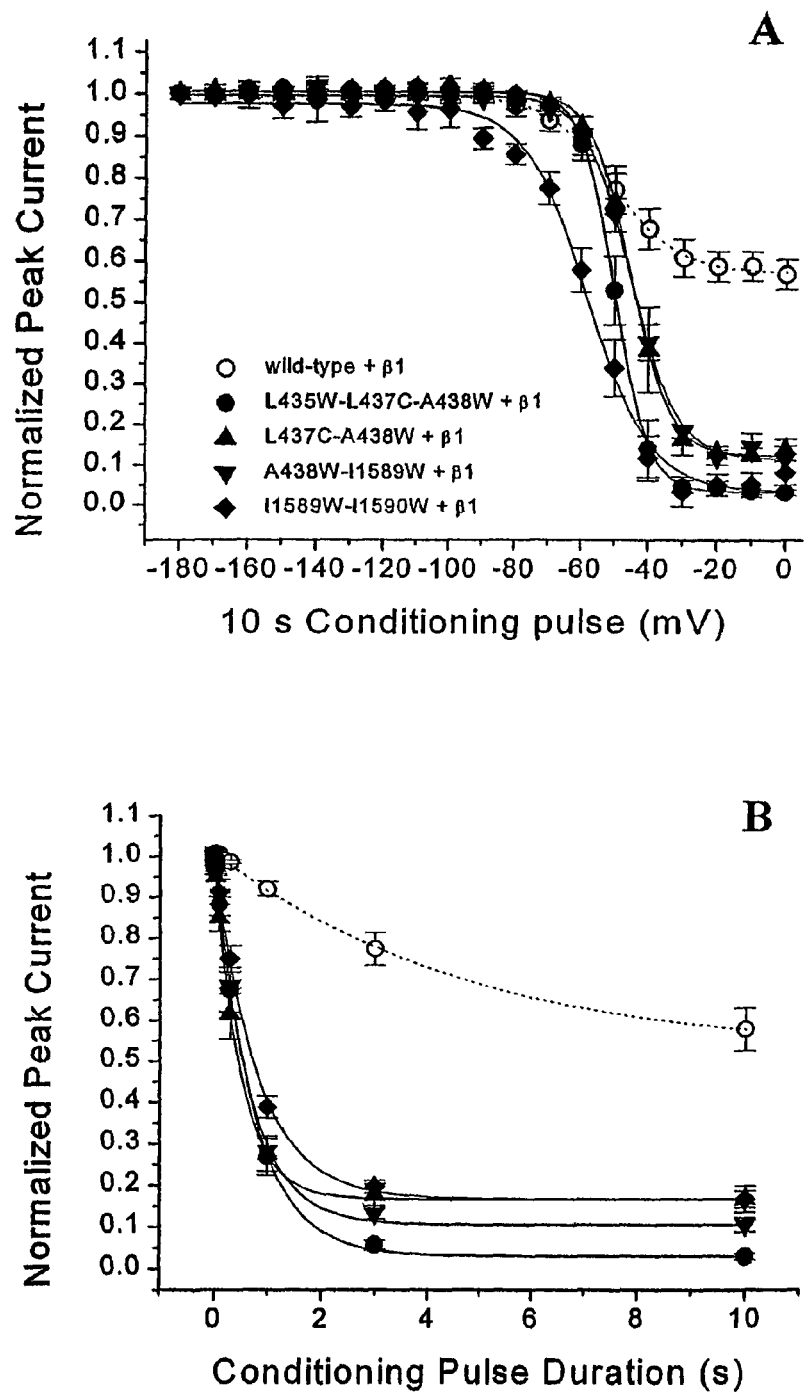
FIGS. 9A-B shows slow inactivation gating of double and triple mutants. Normalized peak current is plotted against conditioning pre-pulse potential for each (A). The development of slow inactivation (B).
Figure 10A:
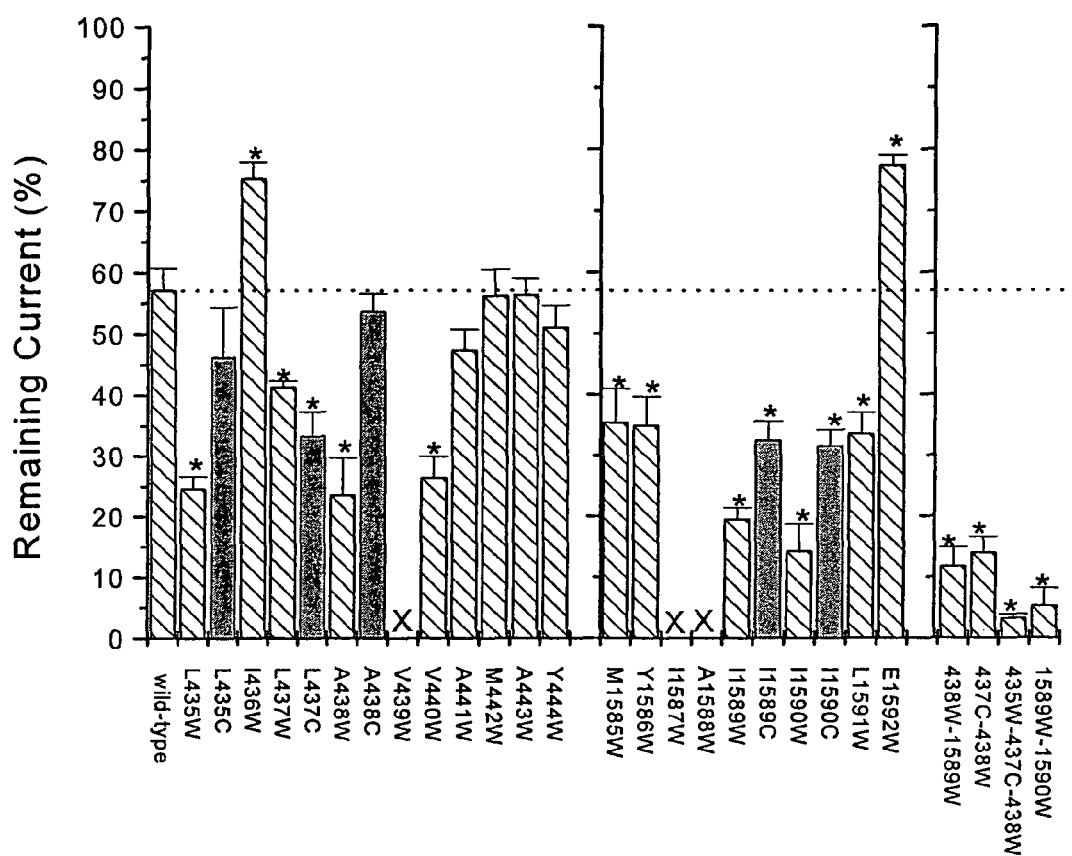
FIG. 10 shows a coarse correlation between fast and slow inactivation gating. (A) The relative level of slow inactivation for D1S6 mutants (left), D4S6 (middle), and double and triple mutants (right). (B) The fraction of slow-inactivated current versus the fraction of noninactivating current of the individual mutant.
Figure 10B:
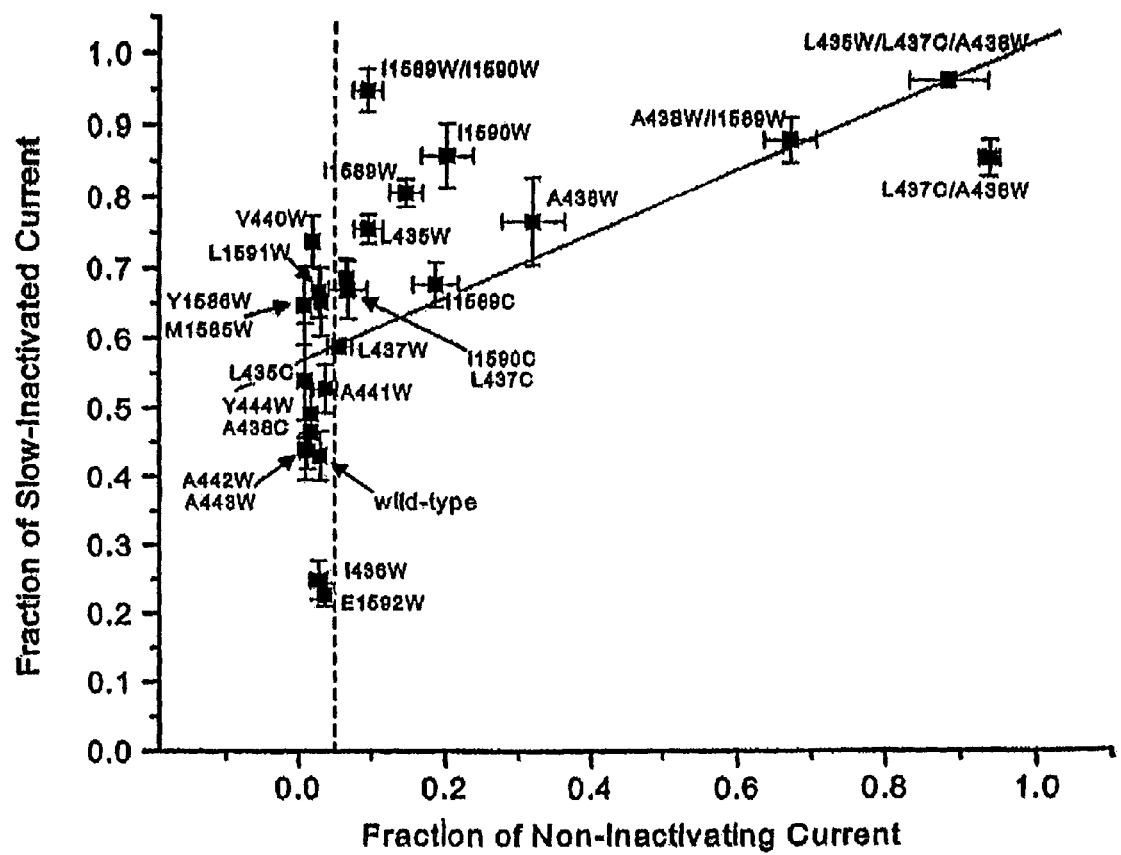
Figure 11:
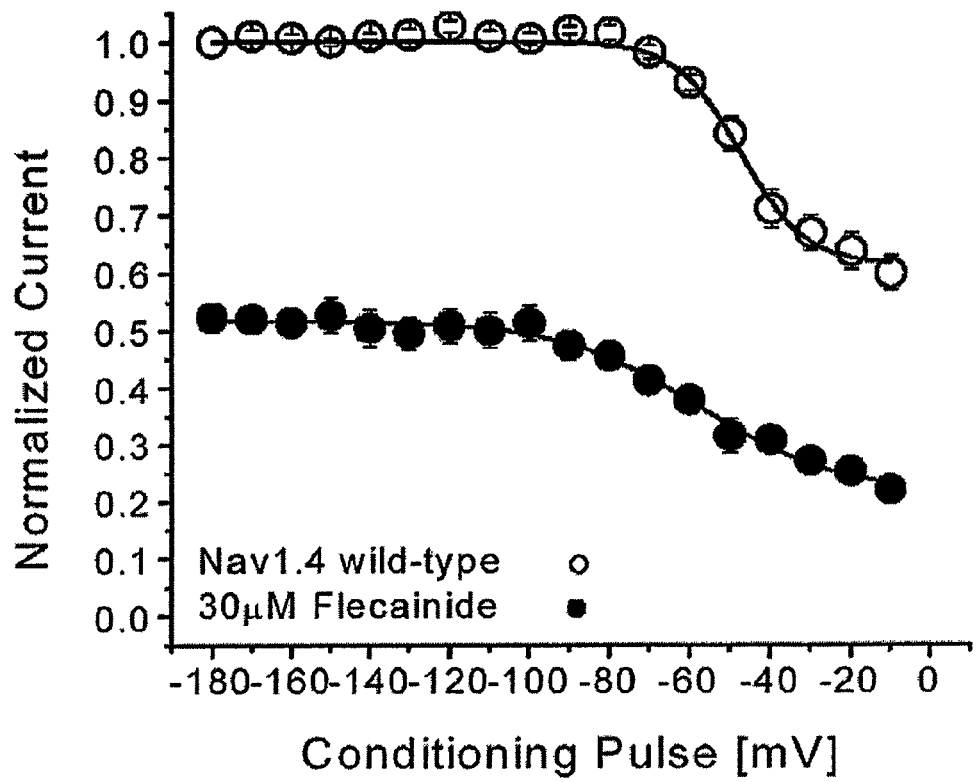
FIG. 11 depicts voltage dependence of flecainide block in rNav1.4 channels.

With a gap of 100 ms at −140 mV, which allowed channels to recover from their fast inactivation but not from their slow inactivation, we observed that 57.1±3.6% (n=5) of wild type Na$^+$ currents were slow inactivated at 0 mV for 10 s (FIG. 9A; open circles). In contrast, almost all L435W/L437C/A438W mutant channels were slow-inactivated (FIG. 9A, closed circles) at 0 mV under these experimental conditions. It appeared that this enhanced slow inactivation is in part due to the enhanced forward rate constant as shown in FIG. 9B. Multiple-substituted mutants with enhanced slow inactivation were inactivated with a rather rapid rate, with a time constant of <1 sec at +30 mV (vs. 4.8 s for wild type). It is noteworthy that slow inactivation in wild type channels does not reach its steady state with a 10-s conditioning pulse even at +30 mV (FIG. 9B). Nonetheless, this pulse protocol allowed us to determine which mutants exhibit altered slow inactivation significantly. In general, we observed that mutants with the most impaired fast inactivation (L435, L437, A438, I1589, I1590) were those with enhanced slow inactivation. In particular, the multiple-substituted mutants, such as L437C/A438W and L435W/L437C/A438W, with the most impaired fast inactivation also had the most enhanced slow inactivation.

The study demonstrates that most mutants with a single W substitution at the C-terminus of D1S6 and D4S6 express observable Na+ currents in HEK293t cells. Substitutions with W in this region alter Na+ channel activation, fast inactivation, and/or slow inactivation gating in varying degrees, dependent on the position of the substitution. Five positions (L435, L437, A438, I1589, and I1590) appear to be closely associated with fast inactivation gating. Two mutants (L437C/A438W and L435W/L437C/A438W) with multiple W or C substitutions exhibit minimal fast inactivation. Interestingly, all mutants with impaired fast inactivation display an enhanced slow inactivation phenotype. The order of the level of the maintained current in D1S6/D4S6 residues is as follows: A438W (31.9%)>I1590W (20.0%)>I1589C (18.6%) >I1589W (14.5%)>L435W (9.5%)>L437C (6.7%)>L437W (5.5%)>wild type (2.9%). The amount of maintained current of L437W and L437C is higher than that of the wild type but it did not reach the level of statistical significance. In comparison, Nav1.2-L421 IC (equivalent to Nav1.4-L437C) has a maintained current of ~10% of the peak current, significantly higher than its wild type (~2%). Evidently, differences in the amount of maintained currents exist between mutants derived from different isoforms. The magnitude of the slow inactivation and the fast inactivation appear to have an apparent inverse relationship. The fraction of slow-inactivated channels followed the order I1590W (85.9%)>I1589W (80.6%) >A438W (76.6%)>L435W (75.5%)>L437W (58.7%)>wild type (43.0%) at 0 mV (FIG. 10); these mutants happened to be five residues with impaired fast inactivation. Furthermore, L435W/L437C/A438W, L437C/A438W, and A438W/I1589W mutants with multiple substitutions have minimal fast inactivation, and they show significantly enhanced slow inactivation (96.8%, 93.2%, and 88.3%, respectively).

FIG. 10 shows a coarse correlation between fast and slow inactivation gating. The relative level of slow inactivation for D1S6 mutants (left), D4S6 (middle), and double and triple mutants (right) is shown in FIG. 10A. Non-expressing mutants are noted with an X. Values represent mean ±S.E. of peak current elicited by a 5 ms test pulse to +30 mV preceded by a 10-s conditioning pulse to 0 mV and a 100 ms interval at −140 mV as described in FIG. 9A. Asterisks indicate significant differences from the wild-type channels as determined by a t test ($p<0.05$). Dotted line indicates the value of wild-type. Bars in gray indicate single C-substitution. The fraction of slow-inactivated current vs. the fraction of non-inactivating current of the individual mutant is shown in FIG. 10B. Data for wild type and mutants were taken from FIG. 4 for x axis and from FIG. 1OA for y axis. The mutants are labeled. The solid line is the linear fit of the complete data set with a correlation coefficient (r) of 0.61. Mutants with impaired fast inactivation (fraction of non-inactivating current >5%) are shown at the right-hand side of the dashed line; all of them show enhanced slow inactivation.

It is surprising to find that the mutants with minimal fast inactivation express as well as the wild type in mammalian cells. Previous reports in the literature indicated that, unlike wild-type $Na^+$ channels, various fast-inactivation deficient mutants at the IFM motif expressed poorly in HEK293 expression system under the same conditions. The inactivation-deficient S6 mutants of the invention are useful tools for future studies, including the establishment of permanent cell lines, the screening for potent open-channel blockers that block persistent opening (e.g. anti-arrhythmic agents), the ion permeation in the persistent open channel, and the detailed studies on direct interactions between drugs and the open channel.

Studies with rNav1.4-L435W/L437C/A438W demonstrated that flecainide binds rapidly and preferentially with the open state but minimally with the resting state. Flecainide is very effective in blocking persistent late Na+ currents as evident from its strong time-dependent block of maintained currents during prolonged depolarization. Flecainide binding with the inactivated state is considerably slower than that with the open state by orders of magnitude. Once the channel is blocked by flecainide, the inactivation gate may stabilize receptor-flecainide complex, as the dissociation rate of flecainide is extremely slow and requires ≧1,000 s (~17 minutes) for the full recovery.

We first measured the Na+ current family at voltages ranging from −60 mV to +50 mV. We then applied 30 mM flecainide externally and measured the Na+ current at +50 mV for 5 ms at a 30-s interval. About 50% of the peak currents were inhibited after flecainide block reached its steady state, usually within 5-7 minutes. We then re-measured the Na+ current family in the presence of 30 mM flecainide and found that the current kinetics remained unchanged and the conductance/voltage curves remained comparable with or without flecainide.

The steady-state inactivation of Na+ channels was measured by a standard two-pulse protocol at a test pulse of +30 mV with various conditioning pulses ranging from −160 mV to −15 mV for 100 ms, with and without flecainide. There was a leftward shift of a few mV and the slope factor appeared less steep.

We applied a voltage scanning protocol ranging from −180 mV to 0 mV to determine whether distinct binding affinities of flecainide exist in rNav1.4 Na+ channels. This pulse protocol consisted of a conditioning pulse at various voltages with a 10-s duration intended for drug binding. It was originally designed to test if inactivated channels have higher "saturable" affinities than resting channels for local anesthetics.

Conditioning prepulses ranging from −180 mV to −10 mV were applied for 10s. After a 100-ms interval at −140 mV, $Na^+$ currents were evoked by a test pulse at +30 mV for 5-ms. Currents recorded before (open circle, n=6) and after 30 μM flecainide (closed circle, n=6) were normalized to the current obtained at the −180 mV conditioning pulse and plotted against the conditioning voltages. Flecainide data were then renormalized at each voltage with respect to the control value without flecainide. Data were fitted with a Boltzmann function ($1/[1+\exp((V_{0.5}-V)/k_E)]$). The average $V_{0.5}$ value and $k_E$ (slope factor) value for the fitted functions were (in mV) −47.9±1.1 and 8.6±0.9, respectively, for control and −57.3±2.7 and 17.6±2.1, respectively, for flecainide.

FIG. 11 shows that flecainide at 30 μM blocks resting channels at a constant level from −180 mV to −100 mV. The block increases continuously from −80 mV to −20 mV.

We measured the dose-response curve of flecainide with a 10-s conditioning pulse at −140 mV, −70 mV, and −20 mV, again at a 30-s interval for the flecainide to reach steady state. Binding at these three voltages for local anesthetics generally represents the resting, closed/inactivated, and open/inactivated affinities, respectively. The measurements at −20 mV, −70 mV, and −140 mV provided $IC_{50}$ values of 13.4±0.3, 21.2±0.4, and 31.9±3.0 mM, respectively. The difference between the high and low flecainide affinities is less than 3-fold. In the case of cocaine, the difference between the resting and inactivated block is 28-fold (250 mM vs. 9 mM).

One possibility for the rightward shift of the voltage dependence of flecainide block is that the inactivated channels interact with the drug rather slowly. This appeared to be the case for the development of the inactivated block at −50 mV with a time constant of 10.9±1.3 s. Once developed, the recovery from this inactivated block by flecainide at 100 mM was also very slow with a time constant of >100 s, as if flecainide was trapped within the channel. Unexpectedly, the amplitude of the Na+ currents continued to increase during this recovery period and reached a level that is 78% to the control amplitude without flecainide. A same slow time course also occurred after the block was developed at +30 mV. Thus, both closed/inactivated and open/inactivated block by flecainide recovered nearly to the level about ~80% of the control value with the same slow time course. These results indicated that the resting block at −140 mV by flecainide is much less than the block normally measured at the 30-s interval. The estimated $IC_{50}$ for the resting block of flecainide in wild-type channels is 355 mM at −140 mV.

To test whether flecainide interacts with the open state of Na+ channels we therefore applied repetitive pulses for channel activation. Repetitive pulses at 5 Hz for 60 pulses elicited additional use-dependent block of flecainide by ~50%. The total duration of depolarization was 1.44 s (0.024×60). Therefore, it appears that flecainide binds to the open state of Na+ channels with a faster rate than that of the inactivated state since the similar long pulse did not elicit a comparable use-dependent block. This being true, keeping the channel open persistently during depolarization enhances the block of flecainide.

Figure 12:
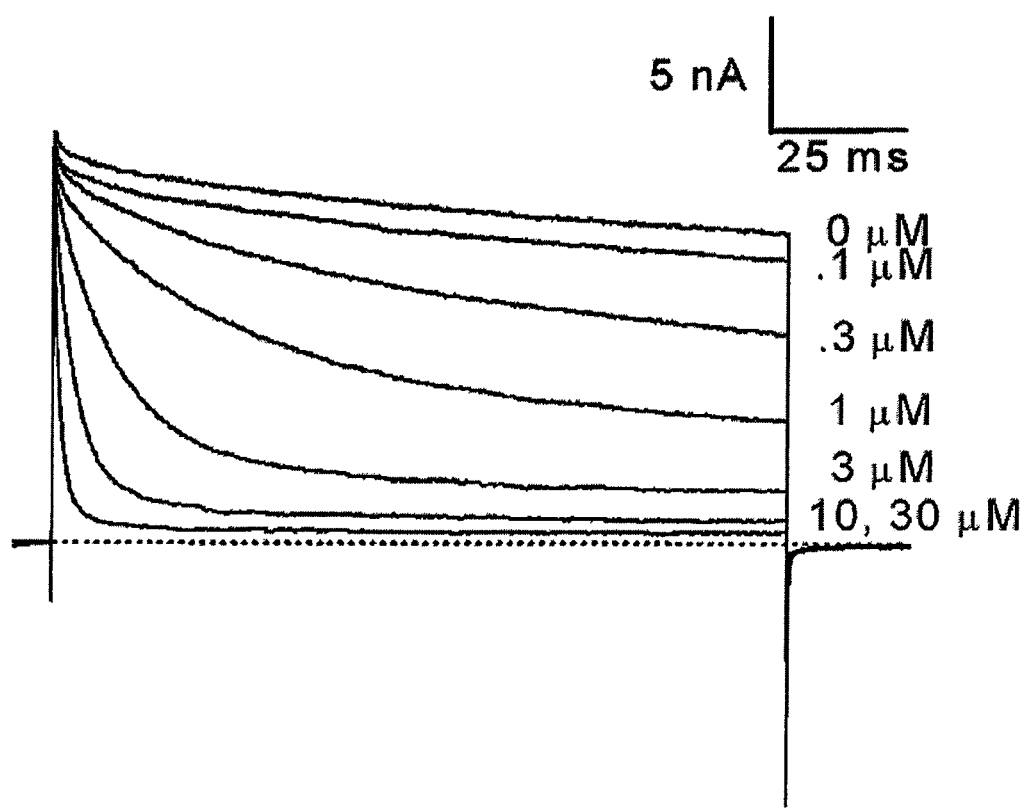
FIG. 12 shows blockade of inactivation-deficient Nav1.4 L435W/L437C/A438W channels at various flecainide concentrations. Superimposed Na$^+$ currents evoked by a 140 ms test pulse to +30 mV every 30 seconds were shown at various flecainide concentrations. Steady state block at each concentration was achieved within 5 min.

To determine interactions between flecainide and the open state directly, we used inactivation-deficient rNav1.4-L435W/L437C/A438W mutant channels of the invention. This mutant channel inactivated minimally during depolarization; instead, a substantial fraction of peak current was maintained. FIG. 12 shows the current families before and after flecainide at various concentrations ranging from 0.1 to 30 μM. At +50 mV, there was a strong time-dependent block of the maintained Na+ currents. This result therefore provides the direct evidence that flecainide binds preferentially with the open state of the Na+ channel and indicates that Nav mutants of the invention can be used as tools for detailed studies on sodium channel block.

Figure 13:
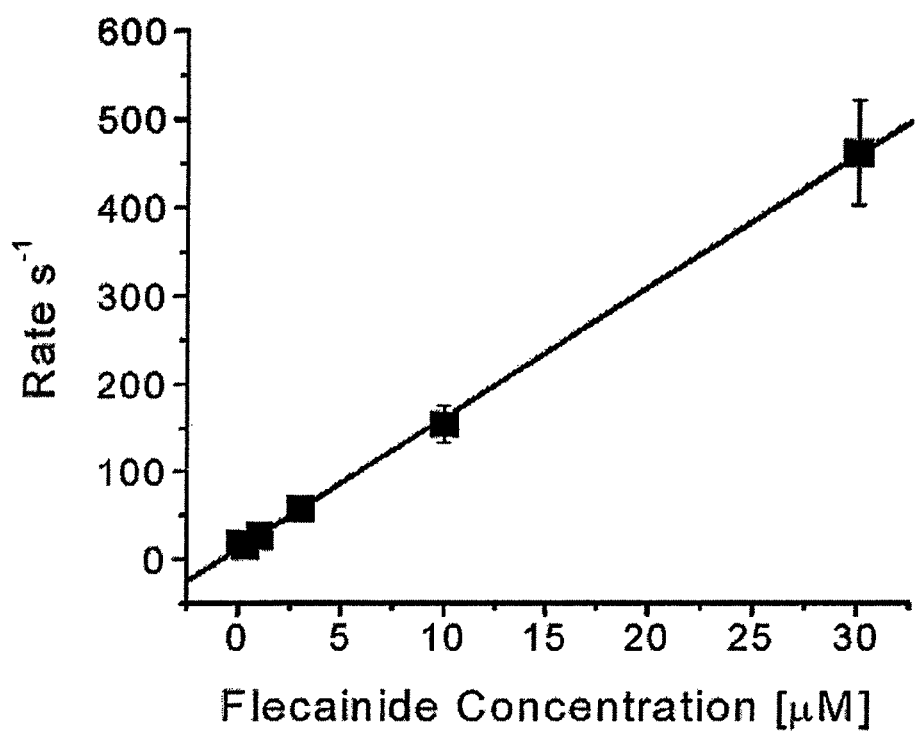
FIG. 13 shows the decay phase of the Na$^+$ current.

We generated non-inactivating Na+ currents using a test pulse of +30 mV and then measured the time-dependent block of flecainide at various concentrations. FIG. 13 shows the decay phase of the Na$^+$ current. The decay phase of the Na+ current could be well fitted with a single exponential function and the time constant (τ) was inverted and plotted against the corresponding concentration. Data were fitted with a linear regression y=14.9x+12.16 solid line). The on-rate and off-rate constant of flecainide with the open channel are estimated to be 14.9 μM$^{-1}$s$^{-1}$ (the slope factor) and 12.2 s$^{-1}$ (y-intercept), respectively. The calculated dissociation constant yields 0.81 μM.

The $IC_{50}$ values for the open (estimated block at the end of the pulse) and the resting block (estimated block at the peak current) were 0.61±0.07 μM and 208.3±16.9 μM, respectively. In contrast, with a conditioning pulse at −50 mV for 10 s, the $IC_{50}$ was 4.1±0.1 μM (estimated block at the peak current) or about 7-fold less potent than that of the open channel block. This suggests channel opening is required for the high-affinity block of flecainide. With limited channel opening around activation threshold of −50 mV, the flecainide affinity is not as high as that of the open channel block.

Repetitive pulses at 5 Hz demonstrate that flecainide produces an additional use-dependent block in the peak current amplitude. It appeared that this rapid phase of the use-dependent block was caused directly by the time-dependent block of the non-inactivating current during the pulse. This time-dependent block recovers little during the 200-ms interpulse at −140 mV. There was also a slow inhibition of peak currents during repetitive pulses in inactivation-deficient channels even without flecainide.

From the foregoing results one may conclude that: (1) Flecainide block of the wild-type Na+ channel developed after channel activation has a very slow recovery time course, up to 10,000 s (or ~17 minutes) at the holding potential of −140 mV. Any pulse protocol that activates Na+ channels at a frequency as low as one per 30 s will significantly perturb the degree of flecainide block. (2) The resting and open channel affinities differ by ~500-fold in the inactivation-deficient mutant channels of the invention (0.61 μM vs. 307 μM, respectively). (3) The recovery from the open channel block by flecainide is relatively fast at −140 mV, with a time constant of 11.2 s in inactivation-deficient mutant channels, or several orders faster than that with intact fast inactivation in wild-type Na+ channels.

Flecainide appears to interact with the resting state of Na+ channels rather weakly. At 100 mM flecainide blocks only about ~20% of peak Na+ currents if the cell is not stimulated repetitively in 1,000 s. The calculated $IC_{50}$ for flecainide block is therefore about 400 μM. It will be difficult to measure this value directly in a single cell having a wild-type Nav protein at various concentrations, since only one test pulse per 17 minutes can be applied for such dose-response assay. In contrast, the $IC_{50}$ for flecainide block of inactivation-deficient mutant Na+ channels of the invention can be estimated directly from the peak current amplitude, which yields 307±19 μM for the resting block.

Flecainide appears to be a rather pure open channel blocker with minimal interactions with resting state. Flecainide has been shown to be beneficial for the treatment of a number of genetic diseases with mutations on the Na+ channel (e.g., Brugada et al., 1999; Windle et al., 2001). Many of these defective channels exhibit persistent late Na+ currents lasting hundreds of milliseconds during prolonged depolarization, such as in the cases of DKPQ (Bennett et al., 1995) or hyperkalemic periodic paralysis (Cannon et al., 1991). Recently, Nagatomo et al (2000) found that flecainide preferentially blocks the late Na+ currents in the DKPQ mutant. The results above demonstrate that flecainide indeed blocks the maintained persistent Na+ currents effectively and rapidly. The therapeutic plasma concentration of flecainide is 0.4 to 2 μM as an antiarrhythmic agent. At this concentration range, a substantial fraction of the persistent late current should be blocked by flecainide, which exhibits an $IC_{50}$ of 0.61 μM for the open channel. The persistent late currents are likely more vulnerable to flecainide block as the peak currents are rapidly inactivated and may not be blocked in time. The open-channel selective blockers, such as flecainide and pilsicainide have broader applications for various pathological conditions that manifest an increase in persistent late Na+ currents in the heart (Saint et al., 1992), in brain (Crill, 1996) or in muscle (Cannon, 1996) and the search for improved agents to treat these pathological conditions is greatly advanced by the screen of the present invention.

Stable expression of hNav1.4-L443C/A444W inactivation-deficient mutant Na$^+$ channels in HEK293 cells The advantages of a permanent mammalian cell line expressing inactivation-deficient mutant Na$^+$ channels are two-fold. First, a permanent cell line would simplify in vitro studies of hNav1.4-L443C/A444W mutant Na$^+$ channels including biophysical studies of the persistent open channel and pharmacological characterizations of drug effects on late Na$^+$ currents. Second, the cell line may be utilized to screen potent open-channel blockers using an automated parallel patch-clamp system (e.g., PatchXpress or Ionworks HT) [Sanguinetti and Bennett, 2003].

Previous attempts to establish IFM/QQQ inactivation-deficient Na$^+$ channels in this cell line suggested that sodium overload from spontaneous channel openings inhibited channel expression [Grant et al., 2000]. In contrast, a relatively high level of expression of inactivation-deficient Na$^+$ channels can be attained over several months in the stably transfected HEK293 cells of the present invention. Several factors may favor the expression of hNav1.4-L443C/A444W mutant Na$^+$ channels in our HEK293 cell line: the enhanced slow inactivation, rightward shifts in activation gating, and/or post-translational modifications.

After transient transfection of an hNav1.4-L443C/A444W clone, HEK293 cells exhibited robust inactivation-deficient Na$^+$ currents. We therefore attempted to establish a stable HEK293 cell line expressing a high level of persistent late Na$^+$ currents.

For preparation of the transfected cells of the present invention, full-length hNav1.4 cDNA inserted in the pRc/CMV vector was obtained from Dr. Theodore Cummins (Indiana University, Indianapolis, Ind.). Mutagenesis of hNav1.4-L443C/A444W cDNA was achieved as described above for the creation of rat skeletal muscle Nav1.4 mutant clones. The mutations occurred at position 21-22 of the D1S6 C-terminus [Wang et al., 2003a].

Human embryonic kidney (HEK293) cells were maintained at 37° C. in a 5% CO$_2$ incubator in DMEM (Life Technologies, Inc., Rockville, Md.) containing 10% fetal bovine serum (HyClone, Logan, Utah), and 1% penicillin and streptomycin solution (Sigma, St. Louis, Mo.). HEK293 cells were transfected with the mutant clone in pRc/CMV vector along with a rat β1 subunit in pcDNA1 by a calcium phosphate precipitation method [Wang et al., 2004]. Transfected HEK293 cells were treated with 1 mg/ml G-418 (Invitrogen, Inc.) during selection in 100-mm culture dishes. The selection DMEM medium contained no penicillin or streptomycin. Individual G-418 resistant colonies were isolated using glass cylinders (i.d.=6 mm) 2 weeks after transfection. Isolated colonies were trypsinized and replated in 35-mm culture dishes each with a gelatin-treated coverslip. The coverslip was removed from the dish after 2-3 days and ≧5 cells from each coverslip were assayed under the whole-cell configuration.

Five positive colonies with inactivation-deficient currents were expanded and frozen individually. One colony was later reestablished and maintained in Ti-25 flasks for studies described here. As expected, this colony did express mRNA of the Nav1.4 α-subunit, but not β1-subunit as determined by PCR. Evidently, without neomycin/G418-resistance gene the β1-pcDNA1 vector was excluded during G-418 selection.

One colony expressing Na$^+$ currents was selected from a total of 5 positive colonies for further studies. Stably transfected cells were reestablished from a frozen vial and were maintained with continuous passages weekly over a period of four months in Ti-25 flasks. It was not necessary to include G-418 in the media once the cell line was reestablished.

The whole-cell configuration of a patch-clamp technique [Hamill et al., 1981] was used to study Na$^+$ currents in stably transfected HEK293 cells at room temperature (22±2° C.). Electrode resistance ranged from 0.5 to 1.0 MΩ. Command voltages were elicited with pCLAMP8 software and delivered by Axopatch 200B (Axon Instrument, Foster City, Calif.). Cells were held at −140 mV and dialyzed for ~10-15 min before current recording. Most of the capacitance and leak currents were cancelled with a patch-clamp device and by P/-4 subtraction. Liquid junction potential was not corrected. Peak currents at +50 mV were ~2-20 nA for the majority of cells. Access resistance was about 1-2 MΩ; series resistance compensation of >85% typically resulted in voltage errors of <4 mV at +50 mV. All current measurements were performed at +30 mV or +50 mV for the outward Na$^+$ currents. Such recordings allowed us to avoid the complication of series resistance artifacts and to minimize inward Na$^+$ ion loading (Cota and Armstrong, 1989). Curve fitting was performed by Microcal Origin (Northampton, Mass.).

Flecainide-HCl, amiodarone-HCl, and mexiletine-HCl were purchased from Sigma (St. Louis, Mo.). (S)-Propafenone-HCl and batrachotoxin (BTX) were generous gifts from Dr. Wolfgang Lindner (Graz, Austria) and Dr. John Daly (Bethesda, Md.), respectively. Antiarrhythmic drugs were dissolved in dimethylsulfoxide (DMSO) as stock solutions and stored at 4° C. Final drug concentrations were made by serial dilution. The highest DMSO concentration in bath solution was 0.1% except for BTX, which contained 1% DMSO in pipette solution. DMSO at a final concentration of 1% had no effect on Na$^+$ currents. Tetrodotoxin was purchased from EMD Biosciences (San Diego, Calif.) and was dissolved in distilled water as stock solution at 1 mM. Cells were perfused with an extracellular solution containing (in mM) 65 NaCl, 85 choline-Cl, 2 CaCl$_2$, and 10 HEPES (titrated with tetramethylammonium-OH to pH 7.4). The pipette (intracellular) solution consisted of (in mM) 100 NaF, 30 NaCl, 10 EGTA, and 10 HEPES (titrated with cesium-OH to pH 7.2).

Figure 14:
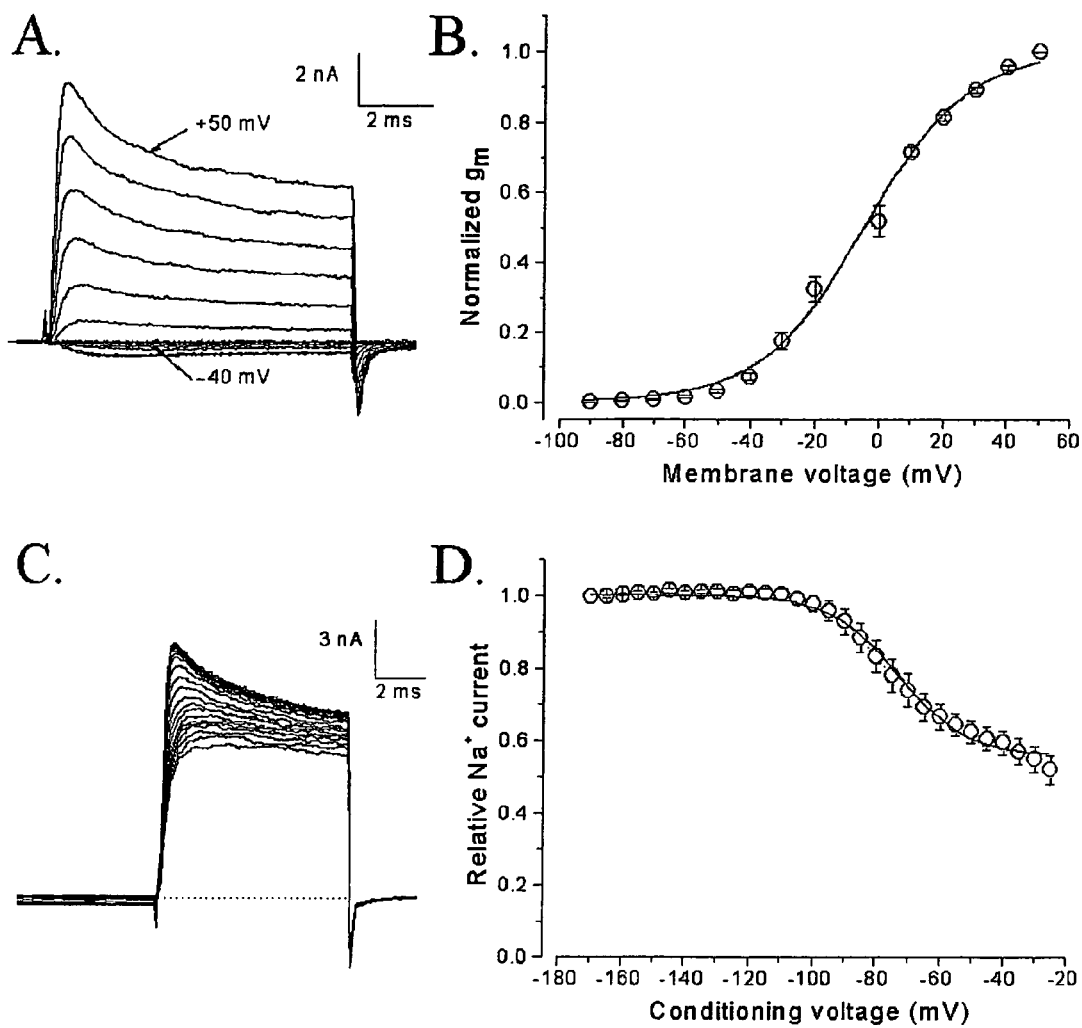
FIGS. 14A-D shows gating properties of hNav 1.4-L443C/A444W mutant channels in stably transfected HEK293 cells. (A) Superimposed Na$^+$current traces evoked by 8-ms pulses to voltages ranging from −100 to +50 mV in 10-mV increments. The inward current evoked by a pulse to −40 mV and the outward current evoked by a pulse to +50 mV are labeled. (B) Conductance plotted against the corresponding voltage. Superimposed current traces evoked by an 8-ms test pulse to +50 mV with 100-ms conditioning pulses, increased in 5-mV increments between −170 and −25 mV. The interval between pulses was 10 seconds. (D) Normalized Na$^+$ current availability (h∞) plotted against conditioning voltage.

FIG. 14A shows a family of superimposed inactivation-deficient Na$^+$ current traces recorded from a cell after 16 passages. The current traces were evoked by 8-ms pulses to voltages ranging from −100 to +50 mV in 10-mV increments. The inward current evoked by a pulse to −40 mV and the outward current evoked by a pulse to +50 mV are labeled. Under our ionic conditions, these currents were activated around −40 mV and reversed around −10 mV.

For FIG. 14B, conductance was determined from the equation $g_m=I_{Na}/(E_m-E_{Na})$, where $I_{Na}$ is the peak current, $E_m$ is the test voltage, and $E_{Na}$ is the estimated reversal potential, and plotted against the corresponding voltage. The plot was fitted with a Boltzmann function. The midpoint voltage ($V_{0.5}$) is −4.2±0.9 mV. The holding potential was −140 mV. The conductance curve arises around −40 mV and has a slope factor of 15.9±0.7 mV with 50% channels activated at −4.2±0.9 mV (n=7).

We also characterized the steady-state fast inactivation by a conventional two-pulse protocol. Superimposed current traces were evoked by an 8-ms test pulse to +50 mV with 100-ms conditioning pulses, increased in 5-mV increments between −170 to −25 mV. The interval between pulses was 10 seconds (FIG. 14C). A fraction of Na$^+$ currents, ~55%, was non-inactivating even with a conditioning pulse at −25 mV for 100 ms (FIG. 14D). Inward Na$^+$ currents remained visible during the 100-ms conditioning pulses from −40 to −25 mV, before the test pulse was applied (FIG. 14C). These gating phenotypes are similar to those obtained by transient transfection of hNav 1.4-L443C/A444W Na$^+$ channels.

To quantify the relative density of Na$^+$ channel expression we measured both the peak Na$^+$ current amplitude and the cell capacitance of individual cells. On average, stably transfected cells expressed 283±58 pA/pF (n=8) of peak Na$^+$ currents at +50 mV. This level of expression is comparable to that of rNav1.4 wild-type Na$^+$ currents in transiently transfected cells (e.g., Nau et al., 2003). Thus, impaired fast inactivation alone apparently did not diminish the expression of these mutant channels in HEK293 cells.

Figure 15:
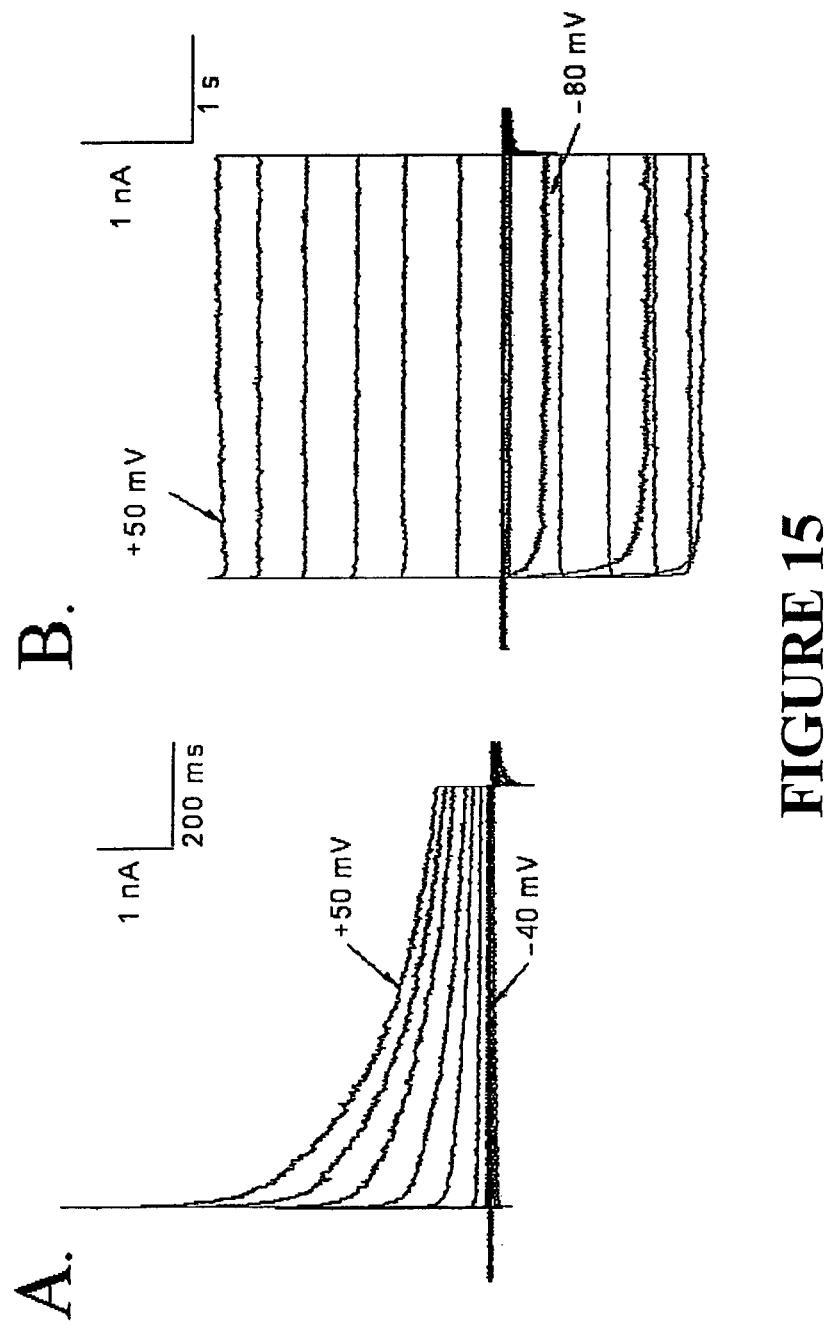
FIGS. 15A-B demonstrates that BTX prevents the slow decay of hNav1.4-L443C/A444W mutant Na$^+$currents.
Figure 16:
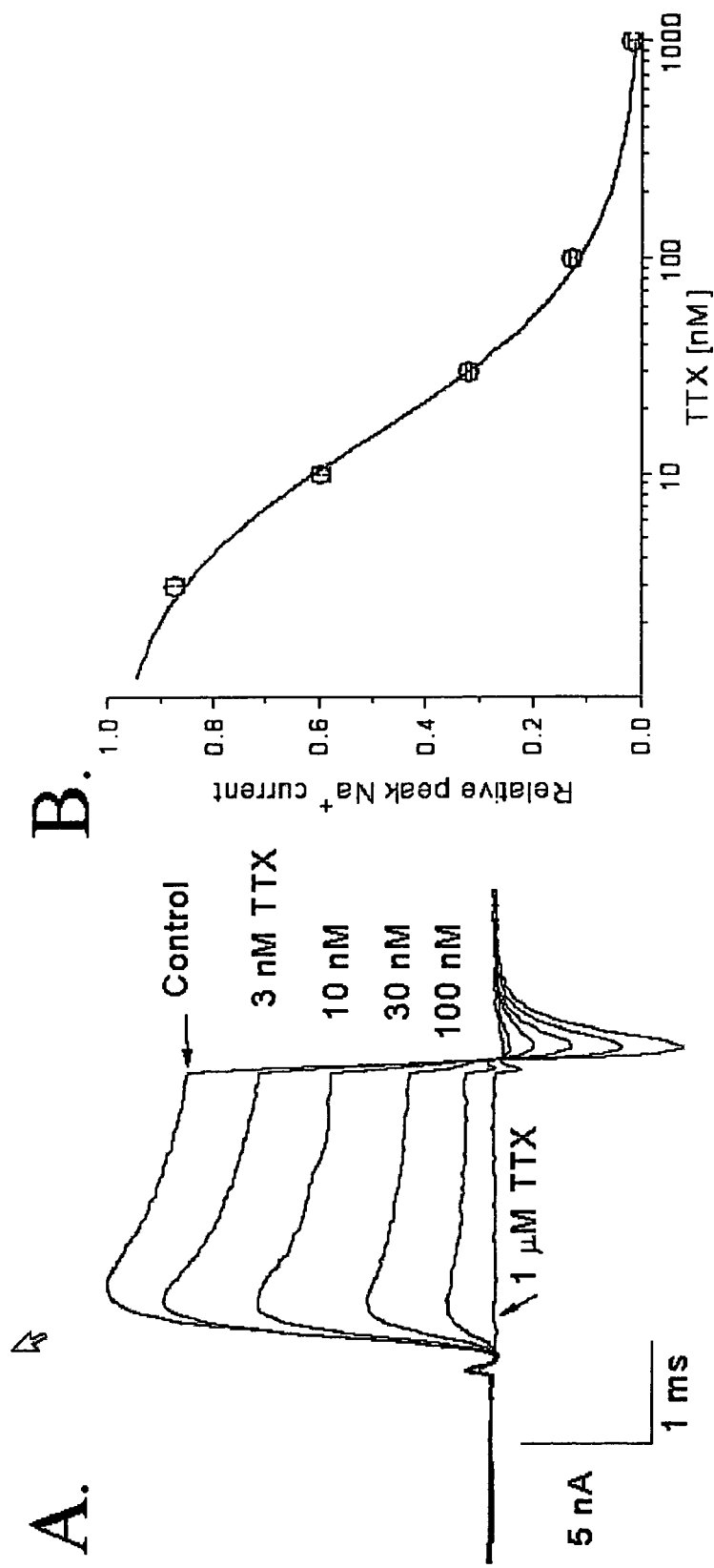
FIG. 16 demonstrates that TTX blocks hNav 1.4-L443C/A444W Na$^+$ channels. (A) Superimposed Na$^+$ current traces were recorded in the absence and in the presence of TTX ranging from 3 nM to 1 μM. Currents were evoked by a 3-ms test pulse to +50 mV every 30seconds. A steady state at each concentration was reached before application of the next concentrated solution. (B) The dose-response curve was constructed using the data set as shown in (A). The peak currents were measured, normalized to the amplitude of the control, and plotted against the TTX concentration. Solid line represents a fit to the data with the Hill equation. The estimated IC$_{50}$ value ± standard error [Hill coefficient ± S.E.] was 15.1 ±0.6 nM [1.09 ±0.04] (n=5).
Figure 17:
FIG. 17 graphically illustrates block of hNav1.4-L443C/A444W Na$^+$ channels by antiarrhythmic drugs. Superimposed Na$^+$currents were recorded before and after 10 μM flecainide (A) and mexiletine (B). Currents of hNav1.4-L443C/A444W Na$^+$channels were evoked by a 100-ms test pulse at +50 mV. Drugs were applied externally. The currents were recorded after the open-channel block reached its steady state, usually within 5 min. A different cell was used in each panel. Holding potential was −140mV.
Figure 18:
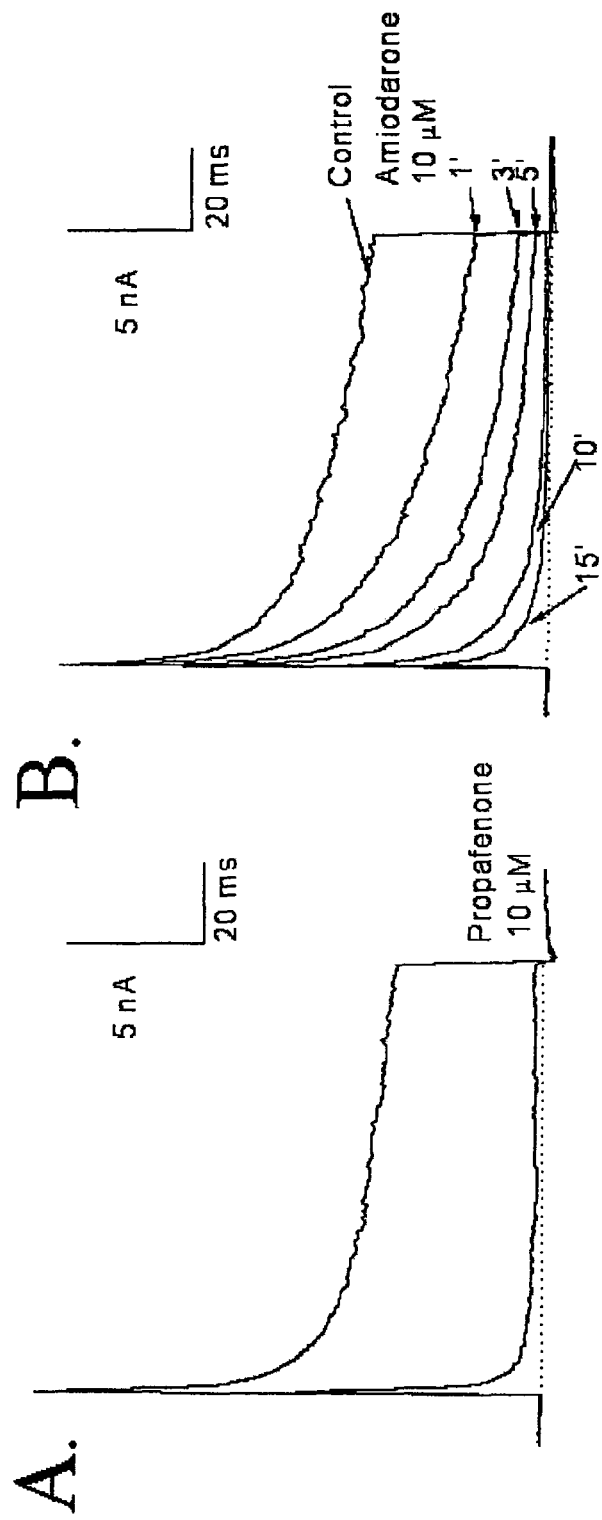
FIG. 18 graphically illustrates the Block of hNav1.4-L443C/A444W Na$^+$ channels by propafenone and amiodarone. Superimposed Na$^+$ currents were recorded before and after 10 μM (S)-propafenone enantiomer (A) and amiodarone (B). Currents of hNav1.4-L443C/A444W Na$^+$ channels were evoked by a 100-ms test pulse at +50 mV. Drugs were applied externally. The currents were recorded after propafenone block reached its steady state, usually within 5 min (A). In contrast, wash-in for amiodarone at 10 μM was slow; Na$^+$ currents were decreased continuously over a period of 15 min (B). A different cell was used in each panel. Holding potential was −140 mV.

Intact receptors in hNav1.4-L443C/A444W inactivation-deficient mutant channels for TTX and BTX To test whether distinct receptors for TTX and BTX at the external surface and within the inner cavity of Na$^+$ channels have been altered, we examined the actions of these ligands in cells expressing hNav1.4-L443C/A444W inactivation-deficient mutant channels. Our data showed that the receptors for TTX and BTX in inactivation-deficient Na$^+$ channels remained intact (FIGS. 15 and 16) with phenotypes similar to their wild-type counterparts. An intact BTX receptor suggests that its binding site within the inner cavity of mutant Na$^+$ channels remains comparable to that of the wild-type channels [Wang and Wang, 2003], whereas an intact TTX receptor indicates that its binding site at the external ion entryway is also comparably normal.

Sensitivity of Inactivation-deficient mutant channels to external BTX

The sensitivity of stably transfected cells expressing inactivation-deficient mutant channels to batrachotoxin (BTX) was examined. FIG. 15A demonstrates that BTX prevents the slow decay of hNav1.4-L443C/A444W mutant $Na^+$ currents. A family of superimposed hNav 1.4-L443C/A444W $Na^+$ current traces was recorded with 800-ms test pulses, ranging from −90 to +50 mV. Initial peak currents were truncated at this slow time scale. Individual current traces at −40 and +50 mV were labeled. During depolarization at voltages between −40 mV to +50 mV, persistent late $Na^+$ currents remained visible even after 800 ms in stably transfected HEK293 cells (FIG. 15A). These late $Na^+$ currents decayed slowly, with a time constant of 258±26 ms at +50 mV (n=5), probably due to an enhanced slow inactivation process [Wang et al., 2003a]. Evidently, hNav1.4-L443C/A444W mutant channels exhibited multiple phases of inactivation dependent on the duration of depolarization applied (FIGS. 14C and 15A).

Previous experiments have demonstrated that BTX eliminates both fast and slow inactivation of wild-type Nav1.4 $Na^+$ channels [Wang and Wang, 1998]. In addition, BTX drastically shifts the activation threshold to the hyperpolarizing direction. We found that inactivation-deficient hNav1.4-L443C/A444W mutant channels remain sensitive to 5 μM BTX applied within the pipette solution. A total of 400 repetitive pulses at +50 mV for 24 ms were first applied at 1 Hz to facilitate BTX binding. Without repetitive pulses, BTX at 5 μM modified very few inactivation-deficient mutant channels, because BTX did not have access to its receptor when the channel was in its closed state. FIG. 15B shows a family of superimposed $Na^+$ current traces from −120 to +50 mV at a slow time frame. Activation of BTX-modified $Na^+$ currents occurred at the threshold of −80 mV (FIG. 15B); once activated, BTX-modified $Na^+$ currents were maintained during 4-s depolarization without evidence of fast or slow inactivation. Because of the leftward shift in activation threshold, large inward $Na^+$ currents were recorded between −80 to −20 mV in BTX-treated cells (FIG. 15B), whereas only small inward $Na^+$ currents were evident between −40 to −20 mV in untreated cells (FIG. 15A). Thus, BTX shifts the activation threshold by −40 mV and completely eliminates the fast and the slow inactivation of these inactivation-deficient hNav1.4-L443C/A444W mutant channels. These BTX phenotypes are similar to those found in wild-type $Na^+$ channels [Wang and Wang, 1998].

Sensitivity of Inactivation-deficient mutant channels to external TTX

External TTX blocks hNav1.4 wild-type $Na^+$ channels with an $IC_{50}$ of 25 nM in frog oocytes [Chahine et al., 1994]. To determine the TTX affinity in inactivation-deficient hNav1.4-L443C/A444W mutant $Na^+$ channels, we constructed the dose-response curve. FIG. 16A shows the superimposed current traces at various external TTX concentrations ranging from 3 nM to 1 μM. TTX blocked these mutant channels potently, with an $IC_{50}$ value of 15.1±0.6 nM (n=5; FIG. 3B) and a Hill coefficient of 1.09±0.04 (n=5) suggesting that, in the hNav1.4-L443C/A444W mutant channel, its external structure near the TTX binding site remains similar to that of the wild-type channel. We found no evidence of a time-dependent block by TTX; both the peak and maintained currents were sensitive to TTX block even during prolonged depolarization.

Open-channel block induced by flecainide and mexiletine during depolarization

Previous reports indicate that persistent late $Na^+$ currents in inactivation-deficient S6 mutant channels are sensitive to block by flecainide and mexiletine in transiently transfected HEK293 cells [Wang et al., 2003b; 2004]. We therefore applied these therapeutic $Na^+$ channel blockers to determine whether they also blocked persistent late $Na^+$ currents in stably transfected HEK293 cells. Persistent late $Na^+$ currents were indeed far more sensitive to flecainide and mexiletine at 10 μM than peak $Na^+$ currents. As a result, a strong block of persistent late $Na^+$ currents by these drugs became evident. FIGS. 17A and B show the blocking characteristics of flecainide and mexiletine, respectively, both at a concentration of 10 μM. Wash-in of these drugs reached their steady-state block of late $Na^+$ currents within 3-5 min. The open-channel blocking phenotypes shown in FIG. 17 are comparable to those reported previously in inactivation-deficient $Na^+$ channels [Wang et al., 2003b, 2004]. These results suggest that hNav1.4-L443C/A444W $Na^+$ channels in stably transfected HEK293 cells interact strongly with flecainide and mexiletine.

By definition, aberrant persistent late $Na^+$ currents created by site-directed mutations, genetic diseases, chemical modifications, or pathological conditions are the results of structural changes of $Na^+$ channels. Could such alterations instigate an increase or a decrease in receptor affinities? This possibility would explain two opposing views on the role of the open-channel block. Unfortunately, direct measurements of the open-channel block in wild type $Na^+$ channels were difficult, if not impossible, because these channels displayed a rather brief open time [Aldrich et al., 1983]. Putting this uncertainty aside, the pressing clinical challenge is to find therapeutic drugs that can silence abnormal late $Na^+$ currents but leave normal transient $Na^+$ currents nearly untouched [Wang DW et al., 1997; Maltsev et al., 2001]. Inactivation-deficient mutant currents in this cell line may be applicable as targets to screen such drugs.

The stably transfected cell line of the present invention is used in an assay to screen a large number of compounds for potent open-channel blockers. We determined the blocking phenotype of (S)-propafenone and amiodarone in inactivation-deficient hNav1.4-L443C/A444W mutant channels. These antiarrhythmic drugs were reported as potent open-channel blockers either in chemically modified inactivation-deficient $Na^+$ channels [Benz and Kohlhardt, 1994] or in late Na+ currents of failing human heart [Maltsev et al., 2001. FIG. 18A shows that (S)-propafenone at 10 μM potently blocks persistent late currents; the block reaches its steady state within 3-5 min. The peak $Na^+$ currents were also inhibited, but to a lesser extent. In contrast, wash-in of amiodarone at 10 μM was relatively slow (FIG. 18B), unlike (S) propaferone and other drugs shown in FIG. 17 at the same concentration. Most, if not all, persistent late currents were inhibited by 10 μM amiodarone over a period of 15 min. The peak currents were also reduced slowly, but again to a lesser extent. Wash-out of amiodarone block was slow and incomplete over a period of ≧min. Together, these results strongly suggest that this cell line expressing hNav1.4-L443C/A444W mutant channels can be used to identify potent open-channel blockers. The fact that at their therapeutic plasma concentration antiarrhythmic mexiletine (2.8-11.2 μM; Roden, 2001), flecainide (0.5-2.4 μM), amiodarone (0.77-3.1 μM), and propafenone (0.5-1.5 μM); [Steurer et al., 1991] effectively block persistent currents in this cell line supports such an assessment. We found that antiarrhythmic flecainide, mexiletine, propaferone, and amiodarone, potently blocked persistent late $Na^+$ currents of inactivation-deficient mutant channels (FIGS. 17 and 18). Previous investigations give two conflicting hypotheses regarding the role of the open-channel block. On the one hand, a quaternary ammonium derivative of lidocaine, QX-314, does not block the inactivation-deficient $Na^+$ currents in pronase-treated $Na^+$ channels [Cahalan, 1978; Yeh, 1978]. In IFM/QQQ mutant channels, the open-channel affinity for lidocaine or cocaine is 3- to 10-fold less than the inactivated-channel affinity [Bennett et al., 1995; O'Leary and Chahine, 2002]. These results all lead to a hypothesis that the inactivated state plays a dominant role in QX-314/lidocaine/cocaine block of $Na^+$ channels, consistent with the modulated receptor hypothesis [Hille, 1977; Hondeghem and Katzung, 1977; Bean et al., 1983]. Results from a weak open-channel block in IFM/QQQ mutant channels by flecainide, RAD-243, and disopyramide [Grant et al., 2000] gave additional support for this hypothesis. On the other hand, local anesthetics and antiarrhythmic drugs potently block persistent late $Na^+$ currents that were generated under different conditions. Among these conditions are (1) chloramine-T-treated squid axons [Wang et al., 1987], (2) mutations that cause genetic diseases [Wang DW et al., 1997; 1999; Nagatomo et al., 2000], (3) hypoxia/failing cardiac myocytes [Ju et al., 1992; 1996; Maltsev et al., 2001], or (4) inactivation-deficient S6 mutants [Wang et al., 2003b; 2004]. These results indicate that the open state of the $Na^+$ channel binds strongly with lidocaine, QX-314, mexiletine, and flecainide and lead to an opposite hypothesis that the open-channel block plays an important therapeutic role in vivo.

The invention claimed is:

1. An isolated nucleic acid encoding a mutant Nav 1.4 or Nav 1.5 protein, wherein said mutant protein differs from wild-type mammalian human or rat Nav1.4 or Nav1.5 by substitution with tryptophan, phenylalanine, tyrosine or cysteine at from one to five positions selected from the group consisting of positions 19, 21 and 22 of the S6 segment of D1 domain and positions 23 and 24 of the S6 segment of the D4 domain, wherein said mutant protein is fast-inactivation deficient.

2. An isolated nucleic acid encoding a rat or human Nav1.4 or Nav1.5 protein that differs from wild-type mammalian human or rat Nav1.4 or Nav1.5 by substitution with tryptophan, phenylalanine, tyrosine or cysteine at from one to five positions selected from the group consisting of positions L435, L437, A438, I1589 and I1590 of rNav1.4, wherein said mutant protein is fast-inactivation deficient.

* * * * *

UNITED STATES PATENT AND TRADEMARK OFFICE
CERTIFICATE OF CORRECTION

| | | |
|---|---|---|
| PATENT NO. | : 7,745,600 B2 | |
| APPLICATION NO. | : 11/507232 | |
| DATED | : June 29, 2010 | |
| INVENTOR(S) | : Sho-Ya Wang | |

It is certified that error appears in the above-identified patent and that said Letters Patent is hereby corrected as shown below:

In the Specification

Col. 1, line 10

STATEMENT REGARDING FEDERALLY SPONSORED RESEARCH OR DEVELOPMENT

Delete "This invention was made under grant number 5RO1HL6607602 from the National Heart, Blood and Lung Institute. The government may have certain rights in the invention."

Insert --This invention was made with government support under grant no. HL066076 awarded by the National Institutes of Health. The government has certain rights in the invention.--

Signed and Sealed this
Fifteenth Day of September, 2015

Michelle K. Lee
*Director of the United States Patent and Trademark Office*